US007432343B2

(12) United States Patent
Batheja et al.

(10) Patent No.: US 7,432,343 B2
(45) Date of Patent: Oct. 7, 2008

(54) DIAGNOSTIC APPLICATION OF MAIL

(75) Inventors: Ameesha D. Batheja, Flemington, NJ (US); George Ho, East Brunswick, NJ (US); Michael D'Andrea, Cherry Hill, NJ (US); David J. Uhlinger, Flemington, NJ (US)

(73) Assignee: Janssen Pharmaceutica N.V. (BG)

( * ) Notice: Subject to any disclaimer, the term of this patent is extended or adjusted under 35 U.S.C. 154(b) by 0 days.

(21) Appl. No.: 11/585,030

(22) Filed: Oct. 23, 2006

(65) Prior Publication Data

US 2007/0099252 A1 May 3, 2007

Related U.S. Application Data

(60) Provisional application No. 60/730,189, filed on Oct. 25, 2005.

(51) Int. Cl.
*A61K 38/04* (2006.01)
*A61K 38/00* (2006.01)
*C07K 5/00* (2006.01)
*C07K 7/00* (2006.01)
*C07K 16/00* (2006.01)
*C07K 17/00* (2006.01)

(52) U.S. Cl. .................................. 530/327; 530/326

(58) Field of Classification Search ........................ None
See application file for complete search history.

(56) References Cited

U.S. PATENT DOCUMENTS

2005/0084916 A1* 4/2005 Reinherz et al. ........... 435/7.23

FOREIGN PATENT DOCUMENTS

WO     WO 2005/102040 A    11/2005

OTHER PUBLICATIONS

Yamamoto Masahiro et al.: "Regulation of Toll/IL-1-Receptor-Mediated Gene Expression by the Inducible Nuclear Protein IkappaBzeta" Nature, Jul. 8, 2004, vol. 430, No. 6996, pp. 218-222, XP002425833.

Kitamura A.H. et al.: "Mail a Novel Nuclear IkappaB Protein That Potentiates LPS-Induced IL-6 Production" Febs Letters, Elsevier, Amsterdam, NL, vol. 485, No. 1, Nov. 17, 2000, pp. 53-56 XP004337768.
Yamazaki S. et al.: "A Novel IkappaB Protein, IkappaB-Zeta, Induced by Proinflammatory Stimuli, Negatively Regulates Nuclear Factor-KappaB in the Nuclei" Journal of Biological Chemistry, American Society of Biolochemical Biologists, Birmingham, US, vol. 276, No. 29, Jul. 20, 2001, pp. 27657-27662, XP002996621.
International Search Report dated May 4, 2007 for International Appln. No. PCT/US2006/041321.
Ito T. et al.: "Transcriptional Regulation of the Mail gene in LPS-stimulated RAW264 Mouse Macrophaages" Gene: An International Journal on Genes and Genomes, Elsevier, Amsterdam, NL, vol. 342, No. 1, Nov. 10, 2004, pp. 137-143, XP004622455.
Kitamura H. et al.: "Bacterial Lipopolysaccharide-induced Expression of the IkappaB Protein Mail in B-lymphocytes and Macrophages" Acrhives of Histology and Cytology, Japan Society of Histological Documentation, Niigata, JP vol. 66, No. 1, 2003, pp. 53-62, XP002996625.
Shiina T. et al.: "Targeted Disruption of Mail, a Nuclear IkappaB Protein, Leads to Severe Atopic Dermatitis-Like Disease" Journal of Biological Chemistry, American Society of Biolochemical Biologists, Birmingham, US, vol. 279, No. 53, Dec. 31, 2004 pp. 55493-55498, XP002996627.
Totzke Gudrun et al.: "A Novel Member of the I Kappa B Family, Human I Kappa B-zeta, Inhibits Transactivation of p65 and its DNA Binding" Journal of Biological Chemistry, vol. 281, No. 18, May 2006, pp. 12645-12654, XP002440291.
Yamazaki, Soh et al.: "Stimulus-Specific Induction of a Novel Nuclear Factor-kappaB Regulator, IkkapaB-zeta, via toll/interleukin-1 receptor is Mediated by MRNA Stabilization" Journal of Biological Chemistry, vol. 280, No. 2, Jan. 14, 2005, pp. 1678-1687 XP002440290.

* cited by examiner

*Primary Examiner*—David J. Blanchard
*Assistant Examiner*—Anne M. Gussow
(74) *Attorney, Agent, or Firm*—Laura Donnelly

(57) ABSTRACT

The present invention provides nucleic acids. Polypeptides, antibodies and cells related to MAIL (Molecule possessing Ankyrin repeats Induced by LPS; or IκB-ζ), a novel member of the IκB family, expressed in LPS stimulated monocytes and uses thereof. The isolated nucleic acids, polypeptides, antibodies and cells of the invention can be used in detection assays, screening methods and drug discovery assays.

1 Claim, 10 Drawing Sheets

Figure 1

|   | 1 | 2 | 3 | 4 |   |
|---|---|---|---|---|---|
|   | 0.75 | 3 | 0 | -4 | -1.5 |
|   | 0.75 | 2.5 | 0 | -1.5 | 0.5 |
|   | 2 | 1 | 0 | 0.75 | 0 |
|   |   | 1.25 | 0.75 | 3.5 | 0.75 |
|   |   | 1.5 | 0.75 | 3.5 | 0.75 | b)

1 2

A

B

C

SEQUENCE LISTING

<160> NUMBER OF SEQ ID NOS: 27

<210> SEQ ID NO 1
<211> LENGTH: 718
<212> TYPE: PRT
<213> ORGANISM: Homo sapiens

<400> SEQUENCE: 1

```
Met Ile Val Asp Lys Leu Leu Asp Asp Ser Arg Gly Gly Glu Gly Leu
 1               5                   10                  15

Arg Asp Ala Ala Gly Gly Cys Gly Leu Met Thr Ser Pro Leu Asn Leu
            20                  25                  30

Ser Tyr Phe Tyr Gly Ala Ser Pro Pro Ala Ala Ala Pro Gly Ala Cys
        35                  40                  45

Asp Ala Ser Cys Ser Val Leu Gly Pro Ser Ala Pro Gly Ser Pro Gly
    50                  55                  60

Ser Asp Ser Ser Asp Phe Ser Ser Ala Ser Ser Val Ser Ser Cys Gly
65                  70                  75                  80

Ala Val Glu Ser Arg Ser Arg Gly Gly Ala Arg Ala Glu Arg Gln Pro
                85                  90                  95

Val Glu Pro His Met Gly Val Gly Arg Gln Gln Arg Gly Pro Phe Gln
            100                 105                 110

Gly Val Arg Val Lys Asn Ser Val Lys Glu Leu Leu Leu His Ile Arg
        115                 120                 125

Ser His Lys Gln Lys Ala Ser Gly Gln Ala Val Asp Asp Phe Lys Thr
    130                 135                 140
```

```
Gln Gly Val Asn Ile Glu Gln Phe Arg Glu Leu Lys Asn Thr Val Ser
145                 150                 155                 160

Tyr Ser Gly Lys Arg Lys Gly Pro Asp Ser Leu Ser Asp Gly Pro Ala
            165                 170                 175

Cys Lys Arg Pro Ala Leu Leu His Ser Gln Phe Leu Thr Pro Pro Gln
        180                 185                 190

Thr Pro Thr Pro Gly Glu Ser Met Glu Asp Val His Leu Asn Glu Pro
    195                 200                 205

Lys Gln Glu Ser Ser Ala Asp Leu Leu Gln Asn Ile Ile Asn Ile Lys
210                 215                 220

Asn Glu Cys Ser Pro Val Ser Leu Asn Thr Val Gln Val Ser Trp Leu
225                 230                 235                 240

Asn Pro Val Val Val Pro Gln Ser Ser Pro Ala Glu Gln Cys Gln Asp
                245                 250                 255

Phe His Gly Gly Gln Val Phe Ser Pro Pro Gln Lys Cys Gln Pro Phe
            260                 265                 270

Gln Val Arg Gly Ser Gln Gln Met Ile Asp Gln Ala Ser Leu Tyr Gln
        275                 280                 285

Tyr Ser Pro Gln Asn Gln His Val Glu Gln Gln Pro His Tyr Thr His
    290                 295                 300

Lys Pro Thr Leu Glu Tyr Ser Pro Phe Pro Ile Pro Gln Ser Pro
305                 310                 315                 320

Ala Tyr Glu Pro Asn Leu Phe Asp Gly Pro Glu Ser Gln Phe Cys Pro
                325                 330                 335

Asn Gln Ser Leu Val Ser Leu Leu Gly Asp Gln Arg Glu Ser Glu Asn
            340                 345                 350

Ile Ala Asn Pro Met Gln Thr Ser Ser Ser Val Gln Gln Gln Asn Asp
        355                 360                 365

Ala His Leu His Ser Phe Ser Met Met Pro Ser Ser Ala Cys Glu Ala
    370                 375                 380

Met Val Gly His Glu Met Ala Ser Asp Ser Ser Asn Thr Ser Leu Pro
385                 390                 395                 400

Phe Ser Asn Met Gly Asn Pro Met Asn Thr Thr Gln Leu Gly Lys Ser
                405                 410                 415

Leu Phe Gln Trp Gln Val Glu Gln Glu Glu Ser Lys Leu Ala Asn Ile
            420                 425                 430

Ser Gln Asp Gln Phe Leu Ser Lys Asp Ala Asp Gly Asp Thr Phe Leu
        435                 440                 445

His Ile Ala Val Ala Gln Gly Arg Arg Ala Leu Ser Tyr Val Leu Ala
    450                 455                 460

Arg Lys Met Asn Ala Leu His Met Leu Asp Ile Lys Glu His Asn Gly
465                 470                 475                 480

Gln Ser Ala Phe Gln Val Ala Val Ala Ala Asn Gln His Leu Ile Val
                485                 490                 495

Gln Asp Leu Val Asn Ile Gly Ala Gln Val Asn Thr Thr Asp Cys Trp
            500                 505                 510

Gly Arg Thr Pro Leu His Val Cys Ala Glu Lys Gly His Ser Gln Val
        515                 520                 525

Leu Gln Ala Ile Gln Lys Gly Ala Val Gly Ser Asn Gln Phe Val Asp
    530                 535                 540

Leu Glu Ala Thr Asn Tyr Asp Gly Leu Thr Pro Leu His Cys Ala Val
545                 550                 555                 560
```

-continued

```
Ile Ala His Asn Ala Val Val His Glu Leu Gln Arg Asn Gln Gln Pro
                565                 570                 575

His Ser Pro Glu Val Gln Glu Leu Leu Leu Lys Asn Lys Ser Leu Val
            580                 585                 590

Asp Thr Ile Lys Cys Leu Ile Gln Met Gly Ala Ala Val Glu Ala Lys
        595                 600                 605

Asp Arg Lys Ser Gly Arg Thr Ala Leu His Leu Ala Ala Glu Glu Ala
    610                 615                 620

Asn Leu Glu Leu Ile Arg Leu Phe Leu Glu Leu Pro Ser Cys Leu Ser
625                 630                 635                 640

Phe Val Asn Ala Lys Ala Tyr Asn Gly Asn Thr Ala Leu His Val Ala
                645                 650                 655

Ala Ser Leu Gln Tyr Arg Leu Thr Gln Leu Asp Ala Val Arg Leu Leu
            660                 665                 670

Met Arg Lys Gly Ala Asp Pro Ser Thr Arg Asn Leu Glu Asn Glu Gln
        675                 680                 685

Pro Val His Leu Val Pro Asp Gly Pro Val Gly Glu Gln Ile Arg Arg
    690                 695                 700

Ile Leu Lys Gly Lys Ser Ile Gln Gln Arg Ala Pro Pro Tyr
705                 710                 715

<210> SEQ ID NO 2
<211> LENGTH: 2157
<212> TYPE: DNA
<213> ORGANISM: Homo sapiens

<400> SEQUENCE: 2
atgattgtgg acaagctgct ggacgacagc cgcggcggag aggggctgcg ggacgcggcg     60
ggcggctgcg gcctcatgac cagcccgctc aacctgagct acttctacgg cgcgtcgccg    120
cccgccgccg ccccgggcgc ctgcgacgcc agctgctcgg tcttgggccc ctcggcgccc    180
ggctcgcccg gctccgactc ctccgacttc tcctctgcct cgtcggtgtc ctcctgcggc    240
gccgtggagt cccggtcgag aggcggcgcc cgcgccgagc gccagccagt tgagcccat     300 atgggggttg gcaggcagca gagaggcccc tttcaaggtg ttcgggtaaa gaactcagtg    360
aaggaactcc tgttgcacat ccgaagtcat aaacagaagg cttctggcca agctgtggat    420
gattttaaga cacaaggtgt gaacatagaa cagttcagag aattgaagaa cacagtatca    480
tacagtggga aaaggaaagg gcccgattcg ttgtctgatg acctgcttg caaaaggcca    540 gctctgttgc attcccaatt tttgacacca cctcaaacac caacgcccgg ggagagcatg    600
gaagatgttc atctcaatga acccaaacag gagagcagtg ctgatctgct tcagaacatt    660
atcaacatta gaatgaatg cagccccgtt ccctgaaca cagttcaagt tagctggctg    720
aaccccgtgg tggtccctca gagctccccc gcagagcagt gtcaggactt ccatggaggg    780
caggtctttt ctccacctca gaaatgccaa ccattccaag tcaggggctc ccaacaaatg    840
atagaccagg cttccctgta ccagtattct ccacagaacc agcatgtaga gcagcagcca    900
cactacaccc acaaaccaac tctggaatac agtccttttc ccataccctcc ccagtccccc    960 gcttatgaac caaacctctt tgatggtcca gaatcacagt tttgcccaaa ccaaagctta   1020
gtttcccttt tggtgatca aagggaatct gagaatattg ctaatcccat gcagacttcc   1080
tccagtgttc agcagcaaaa tgatgctcac ttgcacagct tcagcatgat gcccagcagc   1140
gcctgtgagg ccatggtggg gcacgagatg gcctctgact cttcaaacac ttcactgcca   1200
ttctcaaaca tgggaaatcc aatgaacacc acacagttag ggaaatcact ttttcagtgg   1260
```

```
caggtggagc aggaagaaag caaattggca aatatttccc aagaccagtt tctttcaaag    1320
gatgcagatg gtgacacgtt ccttcatatt gctgttgccc aagggagaag ggcactttcc    1380
tatgttcttg caagaaagat gaatgcactt cacatgctgg atattaaaga gcacaatgga    1440
cagagtgcct ttcaggtggc agtggctgcc aatcagcatc tcattgtgca ggatctggtg    1500
aacatcgggg cacaggtgaa caccacagac tgctggggaa gaacacctct gcatgtgtgt    1560
gctgagaagg gccactccca ggtgcttcag gcgattcaga agggagcagt gggaagtaat    1620
cagtttgtgg atcttgaggc aactaactat gatggcctga ctccccttca ctgtgcagtc    1680
atagcccaca atgctgtggt ccatgaactc agagaaatc aacagcctca ttcacctgaa     1740
gttcaggagc ttttactgaa gaataagagt ctggttgata ccattaagtg cctaattcaa    1800
atgggagcag cggtggaagc gaaggatcgc aaaagtggcc gcacagccct gcatttggca    1860
gctgaagaag caaatctgga actcattcgc ctcttttggg agctgcccag ttgcctgtct    1920
tttgtgaatg caaaggctta caatggcaac actgccctcc atgttgctgc cagcttgcag    1980
tatcggttga cacaattaga tgctgtccgc ctgttgatga ggaagggagc agacccaagt    2040
actcggaact tggagaacga acagccagtg catttggttc ccgatggccc tgtgggagaa    2100
cagatccgac gtatcctgaa gggaaagtcc attcagcaga gagctccacc gtattag       2157

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ccgacttctc ctctgcctcg                                                  20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
tcccaatttt tgacaccacc                                                  20

<210> SEQ ID NO 5
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 5
gguguucggg uaaagaacu                                                   19

<210> SEQ ID NO 6
<211> LENGTH: 17
<212> TYPE: PRT
<213> ORGANISM: Homo sapiens

<400> SEQUENCE: 6

Tyr Ser Gly Lys Arg Lys Gly Pro Asp Ser Leu Ser Asp Gly Pro Ala
```

-continued

```
                1               5                  10                 15
Cys

<210> SEQ ID NO 7
<211> LENGTH: 15
<212> TYPE: PRT
<213> ORGANISM: Homo sapiens

<400> SEQUENCE: 7

Gln Asp Phe His Gly Gly Gln Val Phe Ser Pro Pro Gln Lys Cys
 1               5                  10                 15

<210> SEQ ID NO 8
<211> LENGTH: 16
<212> TYPE: PRT
<213> ORGANISM: Homo sapiens

<400> SEQUENCE: 8

Pro Ala Tyr Glu Pro Asn Leu Phe Asp Gly Pro Glu Ser Gln Phe Cys
 1               5                  10                 15

<210> SEQ ID NO 9
<211> LENGTH: 12
<212> TYPE: PRT
<213> ORGANISM: Homo sapiens

<400> SEQUENCE: 9

Asp Asp Ser Arg Gly Gly Glu Gly Leu Arg Asp Ala
 1               5                  10

<210> SEQ ID NO 10
<211> LENGTH: 13
<212> TYPE: PRT
<213> ORGANISM: Homo sapiens

<400> SEQUENCE: 10

His Glu Leu Gln Arg Asn Gln Gln Pro His Ser Pro Glu
 1               5                  10

<210> SEQ ID NO 11
<211> LENGTH: 12
<212> TYPE: PRT
<213> ORGANISM: Homo sapiens

<400> SEQUENCE: 11

Lys Gly Lys Ser Ile Gln Gln Arg Ala Pro Pro Tyr
 1               5                  10

<210> SEQ ID NO 12
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
caccattgtg gacaagctgc tggac                                         25

<210> SEQ ID NO 13
<211> LENGTH: 25
<212> TYPE: DNA
<213> ORGANISM: Artificial Sequence
<220> FEATURE:
<223> OTHER INFORMATION: Description of Artificial Sequence: Synthetic
```

-continued

```
      primer

<400> SEQUENCE: 13
ctaatacggt ggagctctct gctga                                           25

<210> SEQ ID NO 14
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
caccatgatt gtggacaagc tgctgga                                         27

<210> SEQ ID NO 15
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
ctaatacggt ggagctctct gctga                                           25

<210> SEQ ID NO 16
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
cagaggcagc tcttgg                                                     16

<210> SEQ ID NO 17
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
cagtcctcat cctggc                                                     16

<210> SEQ ID NO 18
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
agccgtttct aaagcgc                                                    17

<210> SEQ ID NO 19
<211> LENGTH: 18
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 19
cacgacacgt tgcgtagg                                                    18

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
tcctgtggca tccacgaaac                                                  20

<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
gaagcatttg cggtggacga t                                                21

<210> SEQ ID NO 22
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
agttctttac ccgaacacc                                                   19

<210> SEQ ID NO 23
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
gggaatctga gaatattgc                                                   19

<210> SEQ ID NO 24
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
gtactcggaa cttggagaa                                                   19

<210> SEQ ID NO 25
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
```

-continued

```
<400> SEQUENCE: 25
gcaauauucu cagauuccc                                                    19

<210> SEQ ID NO 26
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 26
uucuccaagu uccgaguac                                                    19

<210> SEQ ID NO 27
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
ggtggtgtca aaattggga                                                    19
```

DIAGNOSTIC APPLICATION OF MAIL

CROSS REFERENCE TO RELATED APPLICATIONS

This application claims priority of the benefits of the filing of U.S. Application Ser. No. 60/730,189, filed Oct. 25, 2005. The complete disclosures of the aforementioned related U.S. patent application are hereby incorporated herein by reference for all purposes.

FIELD OF THE INVENTION

The present invention relates to nucleic acids and polypeptides encoding MAIL (Molecule possessing Ankyrin repeats Induced by LPS; or IθB-ζ), a novel member of the IθB family, expressed in LPS stimulated monocytes, and uses thereof. The invention further relates to cell lines expressing MAIL nucleic acids and polypeptides, and uses thereof. The invention also relates to kits comprising nucleic acids and polypeptides encoding MAIL as well as antibodies against MAIL polypeptides. The present invention is directed to methods and compositions for the detection and treatment of carcinomas, especially metastatic breast cancer. The present invention is further directed to methods for the identification of compounds, which act as MAIL modulators such as antagonists, agonists and inverse agonists.

BACKGROUND OF THE INVENTION

Lipopolysaccharide (LPS) is a major cell wall component of gram-negative bacteria that potently stimulates inflammation. LPS associates with the circulating LPS binding protein (LBP) and through the CD14-Toll-Like Receptor (TLR) complex in immune cells like monocytes and macrophages, signals the production of many pro-inflammatory cytokines such as IL-Iβ, tumor necrosis factor-α (TNF-α) and IL-6. LPS also stimulates the production of chemokines such as IL-8 and monocyte chemotactic protein-1 (MCP-1). These cytokines and chemokines are important to host immunity and their over-expression can have deleterious consequences such as fatal septic shock. Although other organisms such as staphylococci and *Candida* can also cause this condition, the majority of the septic shock cases are due to infection by gram-negative bacilli (Bone, R. C. Gram-negative sepsis: a dilemma of modern medicine. Clinical Microbiology Reviews 1993, January; 6(1): 57-68; Paterson, R. L.; Webster, N. R. Journal of the Royal College of Surgeons of Edinburgh 2000, 45, 178-182). LPS stimulation through TLR4 results in activation of multiple signaling pathways in the cell, such as the JNK, p38, stress-activated mitogen-activated protein kinases as well as NFκB (Goodell et al., Journal of bacteriology 1985, 162, 391-397; Wright et al., Science 1990, 249, 1431-1433; Paik Y., Hepatology 2003, 37, 1043-1055). Synthetic glucocorticoids like dexamethasone (dex) are potent immunosuppressants and are used for prevention of LPS induced shock in animals (Mills et al., Proceedings of the Society for Experimental Biology and Medicine 1971, 138, 507-511). Dex exerts its anti-inflammatory effects primarily by reducing LPS induced production of pro-inflammatory cytokines such as TNF-α (Waage et al., Immunology 1988, 63, 299-302), IL-6 (Waage et al. European Journal of Immunology 1990, 20, 2439-2443), IL-12p40 (Ma et al., Journal of Immunology 2004, 172, 318-330). Although the mechanism of action is not completely understood, dex regulates transcription as well as the translation of cytokines. By inhibiting NFθB activation and translocation to the nucleus, dex negatively regulates the transcription of proinflammatory cytokines such as IL-6. In human lung fibroblasts, TNF-α induced IL-6 mRNA stability is decreased on dex treatment (Tobler et al., Blood 1992, 79, 45-51). Evidence suggests that dex inhibits TNF-α expression at the translation level (Beutler et al. Science 1986, 232, 977-980; Han et al., Journal of Experimental Medicine 1990, 171, 465-475; Han et al., Journal of Experimental Medicine 1990, 172, 391-394).

Molecules possessing Ankyrin repeats Induced by LPS (MAIL) belongs to the inhibitor protein Iθb family. MAIL was first identified in LPS stimulated cells and shares about 40-44% homology with bcl3 and the IθB proteins (Kitamura et al., FEBS Letters 2000, 485, 53-56). MAIL has since been identified in IL-1β (INAP) induced cells (Haruta et al., Journal of Biological Chemistry 2001, 276, 12485-12488) and MAIL has two splice variants, MAIL-S and MAIL-L (Kitamura et al., FEBS Letters 2000, 485, 53-56). MAIL-S and MAIL-L were also independently discovered and referred to as Iθb-ζ (Yamazaki et al. 2001), and IL-1 inducible nuclear ankyrin repeat protein (INAP) (Haruta et al. 2001) respectively. The human MAIL DNA sequence is provided as SEQ ID NO:2 and the human MAIL-L amino acid sequence is provided as SEQ ID NO:1. Studies involving MAIL over-expression show nuclear localization of the protein (Yamazaki et al. 2001, Haruta et al. 2001). However, in-situ hybridization studies have shown that the intracellular distribution of MAIL is cell type specific. In B lymphocyte rich regions such as the lymphoid follicles and mesenteric lymph nodes in the mouse spleen, MAIL expression is cytoplasmic whereas staining in the macrophages is nuclear (Kitamura et al. Archives of Histology and Cytology 2003, 66, 53-62).

Recent reports analyzing the MAIL promoter suggest that the promoter is induced, in part, by NFκB (Ito et al., Gene 2004, 342, 137-143). MAIL expression is TLR4 dependent. In mice with a mutated tlr4 gene, LPS induced MAIL expression is significantly reduced (Kitamura et al., Journal of Veterinary Medical Science, 2002; Vol. 64, 419-422). Over-expression of MAIL potentiates LPS induced IL-6 expression. MAIL has also been shown to regulate NFθB activity in the nucleus (Kitamura et al. 2000; Haruta et al. 2001; Yamazaki et al. 2001). Cells from MAIL knock-out mice have been shown to have impaired IL-6 production in response to LPS, IL-1βand other TLR agonists. It has been shown that MAIL interacts with the p50 subunit of NFθB and that the MAIL knock-out mice have the same responses to IL-1R/TLR agonists as the NFkB/p50 deficient mice. Abrogation of MAIL expression also resulted in decreased expression of genes such as IL12b and Csf2. MAIL knock-out resulted in decreased expression of LPS induced GM-CSF, IL-12p40, G-CSF, C/EBP-δ and endothelin (Yamamoto et al., Nature 2004, 430, 218-222). MAIL knock-out mice develop severe atopic dermatitis like disease suggesting that MAIL is important for regulation of the immune response (Shiina et al. Immunogenetics 2001, 53, 649-655). Although the exact role of MAIL remains unclear, the protein continues to emerge as an important factor in the regulation of inflammatory responses.

United States patent publication US2002182586, discloses the human MAIL sequence as one of the genes, which may be associated with carcinoma. United States patent publication US2002182586 discloses the use of oncogenic retroviruses, whose sequences insert into the genome of the host organism resulting in carcinoma, allows the identification of host sequences involved in carcinoma. Publication WO0170979 discloses genes associated with ovarian cancer as well as methods of assessing whether a patient is afflicted with ovarian cancer.

There exists a need to identify modulators (agonists, inverse agonists and antagonists) of MAIL. Additionally, there is a need for systems that can be used to test compounds that potentially modulate MAIL gene expression and MAIL protein activity. Identification and testing of such compounds would enable the treatment of various diseases where pro-inflammatory cytokines are implicated, such as inflammation, autoimmune diseases such as Rheumatoid arthritis, Alzheimer's disease, myocardial infarction, Paget's disease, osteoporosis, solid tumors such as renal cell carcinoma, breast, prostate and bladder cancers, certain neurological cancers, as well as B cell malignancies (Trikha et al., Clinical Cancer Research 9, 4653-4665). MAIL antagonists can also be useful in the treatment of chronic inflammatory disorders such as systemic Lupus Erythematosus, Multiple sclerosis, Crohn's disease, transplant rejection, psoriasis, allergic contact dermatitis and other atopic eczemas, rheumatoid arthritis, and chronic inflammatory bowel disease (Asadullah et al., Pharmacological reviews 2003, 55, 241-269).

SUMMARY OF THE INVENTION

The present invention provides an antigenic polypeptide selected from: SEQ ID NO: 6; SEQ ID NO: 7; SEQ ID NO: 8; SEQ ID NO: 9; SEQ ID NO: 10; and SEQ ID NO: 11.

The present invention also provides an antibody which selectively binds to a polypeptide, selected from: SEQ ID NO: 6; SEQ ID NO: 7; SEQ ID NO: 8; SEQ ID NO: 9; SEQ ID NO: 10; and SEQ ID NO: 11.

The invention further provides an antibody, which selectively binds to a polypeptide, selected from: SEQ ID NO: 6; SEQ ID NO: 7; SEQ ID NO: 8; SEQ ID NO: 9; SEQ ID NO: 10; and SEQ ID NO: 11 wherein the antibody is a polyclonal antibody or a monoclonal antibody.

In one general aspect, the invention provides a method of detecting cancer, comprising: a) contacting a tissue sample with at least one antibody selectively binding to a polypeptide selected from: SEQ ID NO: 6; SEQ ID NO: 7; SEQ ID NO: 8; SEQ ID NO: 9; SEQ ID NO: 10; and SEQ ID NO: 11, and b) detecting binding of the antibody in the sample, wherein increased levels of antibody binding in the sample relative to a control indicates cancer in the sample.

In another general aspect, the invention provides a method of detecting a dedifferentiated cell in a tissue sample, comprising: a) contacting a tissue sample with at least one antibody selectively binding to a polypeptide selected from: SEQ ID NO: 6; SEQ ID NO: 7; SEQ ID NO: 8; SEQ ID NO: 9; SEQ ID NO: 10; and SEQ ID NO: 11, and b) detecting binding of the antibody in the sample, wherein increased levels of antibody binding in the sample relative to a control indicates at least one dedifferentiated cell in a tissue sample.

In another aspect, the invention provides a method of detecting cancer in a patient, the method comprising: a) measuring the level of expression of a MAIL marker in a patient sample, and b) measuring the normal level of expression of the MAIL marker in a control non-cancer sample, wherein at least a two-fold elevated expression of the MAIL marker in the patient sample indicates cancer.

The invention also provides a method of detecting cancer in a patient, the method comprising:
  a) measuring the level of expression of a MAIL marker in a patient sample;
  b) measuring the level of at least one inflammatory cytokine in the patient sample, selected from: IL-6, IL-8, IL-10, IL-12p40, MCP-1, and MCP-2;
  c) measuring the normal level of expression of the MAIL marker in a control non-cancer sample, and
  d) measuring the level of at least one inflammatory cytokine in the control sample, selected from: IL-6, IL-8, IL-10, IL-12p40, MCP-1, and MCP-2, wherein at least a two-fold elevated expression of the MAIL marker and an increase in the expression of at least one inflammatory cytokine in the patient sample indicates cancer.

The invention further provides a method of detecting cancer in a patient, the method comprising:
  a) measuring the level of expression of a MAIL marker in a patient sample;
  b) measuring the level of expression at least one MHC class I marker in the patient sample selected from: HLA-A, HLA-B, HLA-C;
  c) measuring the normal level of expression of the MAIL marker in a control non-cancer sample, and
  d) measuring the level of at least one MHC class I marker in the patient sample selected from: HLA-A, HLA-B, HLA-C, wherein at least a two-fold elevated expression of the MAIL marker and a decrease in the expression of at least one MHC class I marker in the patient sample indicates cancer.

In another general aspect, the invention provides a method of detecting cancer in a patient, the method comprising:
  a) measuring the level of expression of a MAIL marker in a patient sample;
  b) measuring the level of at least one MHC class II marker in the patient sample selected from: HLA-DR, HLA-DQ, HLA-DP;
  c) measuring the normal level of expression of the MAIL marker in a control non-cancer sample, and
  d) measuring the level of at least one MHC class II marker in the control sample selected from: HLA-DR, HLA-DQ, HLA-DP, wherein at least a two-fold elevated expression of the MAIL marker and an increase in the expression of at least one MHC class II marker in the patient sample indicates cancer.

Additionally, in some aspects, the invention provides a kit, comprising: an antibody which selectively binds to a polypeptide selected from: SEQ ID NO: 6; SEQ ID NO: 7; SEQ ID NO: 8; SEQ ID NO: 9; SEQ ID NO: 10; and SEQ ID NO: 11.

In another general aspect, the invention provides a method of detecting cancer, comprising:
  a) contacting a tissue sample with at least one antibody selectively binding to a polypeptide selected from: SEQ ID NO: 6; SEQ ID NO: 7; SEQ ID NO: 8; SEQ ID NO: 9; SEQ ID NO: 10; and SEQ ID NO: 11, and
  b) detecting binding of the antibody in the sample, wherein increased levels of antibody binding in the sample relative to a control indicates cancer in the sample, wherein the cancer is selected from: T cell lymphomas, synovial sarcoma, seminoma, rhabdomyosarcoma, Leiomyosarcoma, kidney cancer, fibrosarcoma and Ewings sarcoma, glioma, ovarian yolk sac tumor, melanoma, medulloblastoma, Hodgkin's disease, B cell lymphoma, pancreatic cancer, endometrical cancer, prostate cancer, esophagus cancer, thyroid cancer, skin squamous cell cancer, neuroblastoma, nerve sheath malignant tumor, lung cancer, skin basal cell cancer, urinary bladder, liver cancer, stomach cancer, mesothelioma, gastric cancer, esophageal cancer, cervical cancer, rectal cancer, colon cancer, osteosarcoma, gastro stromal tumor, and breast cancer.

In another general aspect, the invention provides a method of detecting cancer, comprising:
  a) contacting a tissue sample with at least one antibody selectively binding to a polypeptide selected from: SEQ ID NO: 6; SEQ ID NO: 7; SEQ ID NO: 8; SEQ ID NO: 9; SEQ ID NO: 10; and SEQ ID NO: 11, and b) detecting binding of the antibody in the sample wherein increased levels of antibody binding in the sample relative to a control indicates cancer in the sample, wherein the cancer is breast cancer.

In a further general aspect the invention provides a method wherein the detecting step comprises at least one process selected from: ELISA, western blot, immunoprecipitation, IHC, and flow cytometry.

The invention additionally provides a method of decreasing MAIL expression in a cell, comprising: introducing an shRNA molecule into a cell wherein the shRNA molecule binds to a MAIL polynucleotide.

In another aspect the invention provides a method wherein the cell is selected from: a transformed cell, a primary human monocyte, a macrophage and a dendritic cell.

In some aspects the invention further provides a method wherein the shRNA molecule is encoded by a sequence selected from: SEQ ID NO:5, SEQ ID NO:23 and SEQ ID NO:24.

Additionally the invention provides an shRNA molecule of between 19 to 30 nucleic acids in length, wherein the shRNA molecule hybridizes under stringent conditions to a MAIL polynucleotide comprising SEQ ID NO:2.

In other aspects the invention provides an shRNA molecule of between 19 to 30 nucleic acids in length, encoded by a sequence comprising SEQ ID NO:5 wherein the shRNA molecule hybridizes under stringent conditions to a MAIL polynucleotide comprising SEQ ID NO:2.

In some embodiments the invention provides an shRNA molecule of between 19 to 30 nucleic acids in length, comprising SEQ ID NO:5 wherein the shRNA molecule hybridizes under stringent conditions to a MAIL polynucleotide comprising SEQ ID NO:22.

In some aspects the invention provides a method of regulating the expression of an inflammatory cytokine in a cell comprising decreasing a MAIL polypeptide expression by introducing a polynucleotide consisting of SEQ ID NO: 5 into a cell wherein the polynucleotide hybridizes to a MAIL polynucleotide and wherein, the cell is selected from: a transformed cell, a primary human monocyte, a macrophage and a dendritic cell.

The invention further provides a method wherein the inflammatory cytokine is selected from: IL-6, IL-8, IL-10, IL-12p40, MCP-1, and MCP-2.

The invention additionally provides a method of regulating expression of IL-8 in a cell comprising decreasing MAIL polypeptide expression by introducing a nucleotide molecule consisting of SEQ ID NO: 5 into a cell wherein the polynucleotide hybridizes to MAIL and wherein, the cell is selected from: a transformed cell, a primary human monocyte, a macrophage and a dendritic cell.

In other aspects the invention provides a method of regulating expression of MCP-1 in a cell comprising decreasing MAIL polypeptide expression by introducing a nucleotide molecule consisting of SEQ ID NO: 5 into a cell wherein the nucleotide molecule hybridizes to MAIL and wherein, the cell is selected from: a transformed cell, a primary human monocyte, a macrophage and a dendritic cell.

In a further aspect, the invention provides a method of identifying compounds capable of decreasing MAIL expression comprising:

a) providing a cell membrane comprising MAIL or a fragment thereof;

b) contacting the cell membrane with a compound;

c) treating the cell membrane with an antibody directed to a polypeptide selected from: SEQ ID NO: 6; SEQ ID NO: 7; SEQ ID NO: 8; SEQ ID NO: 9; SEQ ID NO: 10; and SEQ ID NO: 11 and d) determining the effect of the compound on the expression of the MAIL.

The invention additionally provides a method, wherein the cell membrane comprises a cell.

The invention further provides a method, wherein the determining step comprises comparing the level of expression of MAIL in the absence of the compound to the level of expression of MAIL in the presence of the compound.

In some another general aspect the invention provides a method of identifying compounds capable of decreasing MAIL expression, comprising the steps of:

a) providing a cell expressing MAIL or fragment thereof;

b) adding a compound to the cell; and c) measuring MAIL mRNA.

The invention further provides a method, wherein the measuring step comprises: comparing the level of expression of MAIL in the absence of the compound to the level of expression of MAIL in the presence of the compound.

In some aspects the invention provides a method of identifying compounds capable of decreasing MAIL expression, comprising the steps of:

a) providing a cell expressing MAIL or fragment thereof;

b) adding a compound to the cell; and c) measuring a MAIL polypeptide.

Additionally the invention provides a method, wherein said measuring step comprises: comparing the level of expression of MAIL in the absence of the compound to the level of expression of MAIL in the presence of the compound.

Other aspects, features and advantages of the invention will be apparent from the following disclosure, including the detailed description of the invention and its preferred embodiments and the appended claims.

BRIEF DESCRIPTION OF THE FIGURES

FIG. 1, MAIL and IL-6 are unregulated in LPS treated monocytes. Primary human monocytes were stimulated with the pro-inflammatory agonists LPS (Column 1), PMA/ionomycin (Column 2), MCP-1 (Column 3), IL-1β (Column 4) and TNF-α (Column 5) respectively. Transcription profiling was performed on an in-house developed Target microarray chip (as described in Example 1 infra). Fold changes upon treatment over control were calculated using the OmniViz Pro data analysis software. MAIL expression (Row C) was found upregulated in LPS stimulated cells. Rows A and B show expression of TNF-α factor RNA. IL-6 expression in response to treatment is shown in Rows D and E. Number shown in each box represents a close approximate of the (log) fold change in gene expression upon treatment with the inflammatory agonists. For example, a value shown as 1.5 can range from 1.5 to 2.5 (log) fold. Darker shading of the boxes represents an increase in gene expression approximately equally to the (log) fold change in gene expression upon treatment with the inflammatory agonists.

DETAILED DESCRIPTION

Figure 2:
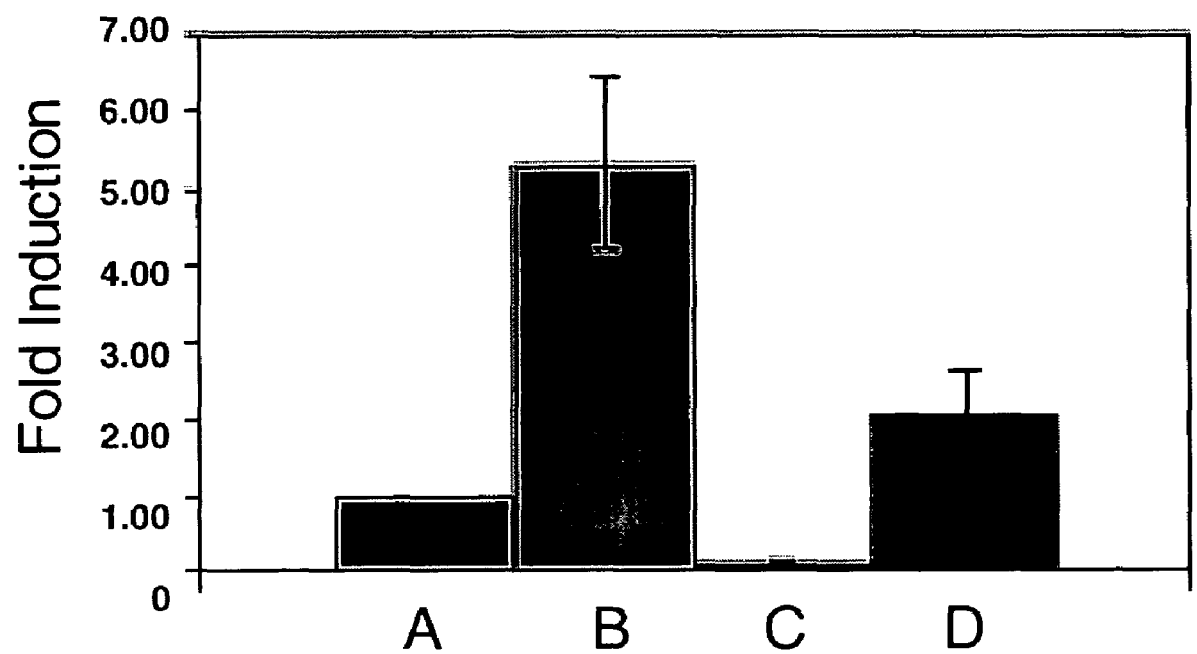
FIG. 2, MAIL short hairpin RNA (shRNA) knocks down basal and LPS induced IL-6 by 50-75%. Primary human monocytes were transfected with either vector alone (Sample A) or MAIL-pSil (Sample C) and treated with LPS for 4 hours post transfection (Sample B and Sample D respectively). Secreted IL-6 in culture supernatants was quantitated using ELISA.

All publications cited herein are hereby incorporated by reference. Unless defined otherwise, all technical and scientific terms used herein have the same meaning as commonly understood to one of ordinary skill in the art to which this invention. As used herein, the terms "comprising", "containing", "having" and "including" are used in their open, non-limiting sense.

The following are abbreviations that are at times used in this specification:
  dex=dexamethasone
  ELISA=enzyme-linked immunoabsorbent assay
  GMCSF=Granulocyte-macrophage colony-stimulating factor
  GCSF=Granulocyte colony stimulating factor
  HTS=High Throughput Screening
  IHC=Immunohistochemistry
  IθB=Inhibitor θB
  Iθ-α-ζ=Inhibitor κB-alpha
  IθB-ε=Inhibitor κB-epsilon
  IθB-ζ=Inhibitor κB-zeta
  IL Interleukin
  INAP=IL-1-inducible Nuclear Ankyrin repeat Protein
  JNK=Jun amino-terminal kinase
  kb=kilobase; 1000 base pairs
  KLH=keyhole limpet hemocyanin
  LC MS/MS=Liquid Chromatography Mass Spectrometrey Mass Spectrometrey
  LBP=LPS binding protein
  LPS=Lipopolysaccharide
  MAIL=Molecule Possessing Ankyrin Repeats Induced by LPS
  MAIL-S=Molecule Possessing Ankyrin Repeats Induced by LPS-Short
  MAIL-L=Molecule Possessing Ankyrin Repeats Induced by LPS-Long
  MCP-1=Monocyte Chemotactic Protein-1
  MCP-2=Monocyte Chemotactic Protein-2
  NFκB=Nuclear Factor κB
  PAGE=polyacrylamide gel electrophoresis
  PCR=polymerase chain reaction
  RT-PCR=Reverse transcription-polymerase chain reaction
  SDS=sodium dodecyl sulfate
  shRNA=short hairpin RNA
  siRNA=small interfering RNA
  SSC=sodium chloride/sodium citrate
  TLR=Toll-like Receptor
  TNF-α=Tumor Necrosis Factor-alpha
  UTR=untranslated region "An activity", "a biological activity", or "a functional activity" of a polypeptide or nucleic acid refers to an activity exerted by a polypeptide or nucleic acid molecule as determined in vivo, or in vitro, according to standard techniques. Such activities can be a direct activity, such as an association with or an enzymatic activity on a second protein or a metal ion-enzyme complex, or an indirect activity, such as a cellular signaling activity mediated by interaction of the protein with one or more than one additional protein or other molecule(s), including but not limited to, interactions that occur in a multi-step, serial fashion.

A "biological sample" or "sample" as used herein refers to a sample containing or consisting of cell or tissue matter, such as cells, cell associated body fluids, biological fluids, culture supernatants or DNA, RNA, or protein isolated from a subject or patient. The "subject" can be bacteria, yeast, arthropods, a mammal, such as a rat, a mouse, a monkey, a human, or any other organism, that has been the object of treatment, observation or experiment. Examples of biological samples include, for example, sputum, blood, blood cells (e.g., white blood cells), amniotic fluid, plasma, semen, bone marrow, tissue or fine-needle biopsy samples, urine, peritoneal fluid, pleural fluid, and cell cultures. Biological samples can also include sections of tissues such as frozen sections taken for histological purposes.

A "test biological sample" or "patient sample" is the biological sample that has been the object of analysis, monitoring, or observation. A "control biological sample" or "control sample" can be either a positive or a negative control for the test biological sample or patient sample. Often, the control biological sample or control sample contains the same type of tissues, cells and/or biological fluids of interest as that of the test biological sample or patient sample.

A "cell" refers to at least one cell or a plurality of cells appropriate for the sensitivity of the detection method. Cells suitable for the present invention can be bacterial, other prokaryotes or eukaryotes.

Examples of cell-associated body fluids include blood fluids (e.g. whole blood, blood serum, blood having platelets removed there from, etc.), lymph, ascitic fluids, gynecological fluids (e.g. ovarian, fallopian, and uterine secretions, menses, vaginal douching fluids, fluids used to rinse cervical cell samples, etc.), cystic fluid, urine, saliva and fluids collected by peritoneal rinsing (e.g. fluids applied and collected during laparoscopy or fluids instilled into and withdrawn from the peritoneal cavity of a human patient). In some embodiments, the level of expression of the marker can be assessed by assessing the amount (e.g. absolute amount or concentration) of the marker in a cell-associated body fluid obtained from a patient. The fluid can, of course, be subjected to a variety of well-known post-collection preparative and storage techniques (e.g. storage, freezing, ultrafiltration, concentration, evaporation, centrifugation, etc.) prior to assessing the amount of the marker in the fluid.

The term "MAIL" as used herein refers to a Molecule possessing Ankyrin repeats Induced by LPS; or I$\theta$B-$\zeta$), a novel member of the I$\theta$B family, expressed in LPS stimulated monocytes. The term "MAIL" can be additionally used to refer to the DNA and RNA which code for proteins of a Molecule possessing Ankyrin repeats Induced by LPS; or I$\theta$B-$\zeta$.

The term "monocyte" as used herein refers to any mononuclear phagocyte circulating in blood that is capable of emigrating into tissue and differentiating into a macrophage.

The term "dendritic cell" as used herein refers to a monocyte derived cell expressing the CD1a+, CD4+, CD11c+, CD40+, CD86+, HLA-DR+ phenotype.

The term "macrophage" as used herein refers to a phagocytic cell of mammalian tissues, derived from a monocyte. Macrophages from different sites have distinctly different properties. The main examples are peritoneal and alveolar macrophages, tissue macrophages (histiocytes), Kupffer cells of the liver and osteoclasts. In response to foreign materials macrophages can become stimulated or activated. Macrophages play an important role in killing of some bacteria, protozoa and tumour cells, release substances that stimulate other cells of the immune system and are involved in antigen presentation. Macrophages can further differentiate within chronic inflammatory lesions to epitheloid cells, or can fuse to form foreign body giant cells or Langhans giant cells.

The term "Lipopolysaccharide" or "LPS" as used herein refers to any and all of the major constituents of the cell walls of gram-negative bacteria. Lipopolysaccharide is highly immunogenic and stimulates the production of endogenous pyrogen interleukin-1, IL-6 and tumor necrosis factor.

The term "cytokine" as used herein refers to small proteins or biological factors (which can be in the range of 5-80 kD) that are released by cells and have specific effects on cell to cell interaction, communication and behavior of other cells, many times including the cytokine producing cell itself.

The term "inflammatory cytokine" as used herein refers to a subset of cytokines involved in inflammation including for example, and not limited to IL-6, IL-8, IL-10, IL-12p40, MCP-1, and MCP-2.

The term "chemokine" as used herein refers to a class of pro-inflammatory cytokines that have the ability to attract and activate leukocytes also known as white blood cells. Chemokines can be divided into at least three structural branches: c (chemokines, c), cc (chemokines, cc), and cxc (chemokines, cxc), according to variations in a shared cysteine motif.

A "clone" is a population of cells derived from a single cell or common ancestor by mitosis. A "cell line" is a primary cell, that derives clonal expansion of cells and is capable of stable growth in vitro for many generations.

A "DNA clone" is a section of DNA that has been copied, isolated or removed from a host and inserted into a vector molecule, such as a plasmid or a phage, or a chromosome, and then replicated to form many identical copies.

The term "cDNA" as used herein means complementary DNA (cDNA) Synthetic DNA reverse transcribed from a specific RNA through the action of the enzyme reverse transcriptase. DNA synthesized by reverse transcriptase using RNA as a template.

A "gene" is a segment of DNA involved in producing a peptide, polypeptide, or protein, and the mRNA encoding such protein species, including the coding region, non-coding regions preceding ("5'UTR") and following ("3'UTR") the coding region. A "gene" can also include intervening non-coding sequences ("introns") between individual coding segments ("exons"). "Promoter" means a regulatory sequence of DNA that is involved in the binding of RNA polymerase to initiate transcription of a gene. Promoters are often upstream ("5'to") the transcription initiation site of the gene. A "regulatory sequence" refers to the portion of a gene that can control the expression of the gene. A "regulatory sequence" can include promoters, enhancers and other expression control elements such as polyadenylation signals, ribosome binding site (for bacterial expression), and/or, an operator. An "enhancer" means a regulatory sequence of DNA that can regulate the expression of a gene in a distance- and orientation-independent fashion. Enhancers can be located upstream, downstream, or even within the gene the enhancer controls. A "coding region" refers to the portion of a gene that encodes amino acids and the start and stop signals for the translation of the corresponding polypeptide via triplet-base codons.

"Nucleic acid sequence" or "nucleotide sequence" refers to the arrangement of either deoxyribonucleotide or ribonucleotide residues in a polymer in either single- or double-stranded form. Nucleic acid sequences can be composed of natural nucleotides of the following bases: thymidine, adenine, cytosine, guanine, and uracil; abbreviated T, A, C, G, and U, respectively, and/or synthetic analogs. Synthetic analogs can include nucleotide and nucleoside analogs as well as non-nucleotide and non-nucleoside analogs.

The term "oligonucleotide" refers to a single-stranded DNA or RNA sequence of a relatively short length, for example, less than 100 residues long. For many methods, oligonucleotides of about 16-25 nucleotides in length are useful, although longer oligonucleotides of greater than about 25 nucleotides can sometimes be utilized. Some oligonucleotides can be used as "primers" for the synthesis of complimentary nucleic acid strands. For example, DNA primers can hybridize to a complimentary nucleic acid sequence to prime the synthesis of a complimentary DNA strand in reactions using DNA polymerases. Oligonucleotides are also useful for hybridization in several methods of nucleic acid detection, for example, in Northern blotting or in situ hybridization.

A "polypeptide sequence" or "protein sequence" refers to the arrangement of amino acid residues in a polymer. Polypeptide sequences can be composed of the standard 20 naturally occurring amino acids, in addition to rare amino acids and synthetic amino acid analogs. Shorter polypeptides are generally referred to as peptides.

An "isolated" nucleic acid molecule is one that is separated from other nucleic acid molecules present in the natural source of the nucleic acid. An "isolated" nucleic acid molecule can be, for example, a nucleic acid molecule that is free of at least one of the nucleotide sequences that naturally flank the nucleic acid molecule at its 5' and 3' ends in the genomic DNA of the organism from which the nucleic acid is derived. Isolated nucleic acid molecules include, without limitation, separate nucleic acid molecules (e.g., cDNA or genomic DNA fragments produced by PCR or restriction endonuclease treatment) independent of other sequences, as well as nucleic acid molecules that are incorporated into a vector, an autonomously replicating plasmid, a virus (e.g., a retrovirus, adenovirus, or herpes virus), or into the genomic DNA of a prokaryote or eukaryote. In addition, an isolated nucleic acid molecule can include a nucleic acid molecule that is part of a hybrid or fusion nucleic acid molecule. An isolated nucleic acid molecule can be a nucleic acid sequence that is: (i) amplified in vitro by, for example, polymerase chain reaction (PCR); (ii) synthesized by, for example, chemical synthesis; (iii) recombinantly produced by cloning; or (iv) purified, as by cleavage and electrophoretic or chromatographic separation.

An "isolated" or "purified" protein or biologically active portion thereof is substantially free of cellular material or other contaminating proteins from the cell or tissue source from which the protein is derived, or substantially free of chemical precursors or other chemicals when chemically synthesized. The language "substantially free of cellular material" includes preparations of protein in which the protein is separated from cellular components of the cells from which the protein is isolated or recombinantly produced. Thus, protein that is substantially free of cellular material includes preparations of protein having less than about 30%, 20%, 10%, or 5% (by dry weight) of heterologous protein (also referred to herein as a "contaminating protein"). When the protein or biologically active portion thereof is recombinantly produced, the protein is also preferably substantially free of culture medium, i.e., culture medium represents less than about 20%, 10%, or 5% of the volume of the protein preparation. When the protein is produced by chemical synthesis, the protein is preferably substantially free of chemical precursors or other chemicals, i.e., the protein is separated from chemical precursors or other chemicals that are involved in the synthesis of the protein. Accordingly such preparations of the protein have less than about 30%, 20%, 10%, 5% (by dry weight) of chemical precursors or compounds other than the polypeptide of interest. Isolated biologically active polypeptide can have several different physical forms. An isolated polypeptide can exist as a full-length nascent or unprocessed polypeptide, or as a partially processed polypeptide or as a combination of processed polypeptides. The full-length nascent polypeptide can be postranslationally modified by specific proteolytic cleavage events that result in the formation of fragments of the full-length nascent polypeptide. The full length protein or fragments of the polypeptide can be chemically modified. A fragment, or physical association of fragments can have the biological activity associated with the full-length polypeptide; however, the degree of biological activity associated with individual fragments can vary. An isolated or substantially purified polypeptide, can be a polypeptide encoded by an isolated nucleic acid sequence, as well as a polypeptide synthesized by, for example, chemical synthetic methods, and a polypeptide separated from biological materials, and then purified, using conventional protein analytical or preparatory procedures, to an extent that permits the polypeptide to be used according to the methods described herein.

The term "recombinant" refers to a nucleic acid, a protein encoded by a nucleic acid, a cell, or a viral particle, that has been modified using molecular biology techniques to something other than its natural state. For example, recombinant cells can contain a nucleotide sequence that is not found within the native (non-recombinant) form of the cell or can express native genes that are otherwise abnormally expressed, under-expressed, or not expressed at all. Recombinant cells can also contain genes found in the native form of the cell wherein the genes are modified and re-introduced into the cell by artificial means. The term also encompasses cells that contain an endogenous nucleic acid molecule that has been modified without removing the nucleic acid from the cell; such modifications include those obtained, for example, by gene replacement, and site-specific mutation.

A "recombinant host cell" is a cell that has had introduced into the cell a recombinant DNA sequence. Recombinant DNA sequence can be introduced into host cells using any suitable method including, for example, electroporation, calcium phosphate precipitation, microinjection, transformation, biolistics "gene-gun" and viral infection. Recombinant DNA may or may not be integrated (covalently linked) into chromosomal DNA making up the genome of the cell. For example, the recombinant DNA can be maintained on an episomal element, such as a plasmid. Alternatively, with respect to a stably transformed or transfected cell, the recombinant DNA has become integrated into the chromosome so that the DNA is inherited by daughter cells through chromosome replication. This stability is demonstrated by the ability of the stably transformed or transfected cell to establish cell lines or clones comprised of a population of daughter cells containing the exogenous DNA. Recombinant host cells can be prokaryotic or eukaryotic, including bacteria such as *Pseudomonas* auerginosa, *E. coli*, fungal cells such as yeast, mammalian cells such as cell lines of human, bovine, porcine, monkey and rodent origin, and insect cells such as *Drosophila*-and silkworm-derived cell lines. It is further understood that the term "recombinant host cell" refers not only to the particular subject cell, but also to the progeny or potential progeny of such a cell. Because certain modifications can occur in succeeding generations due to either mutation or environmental influences, such progeny may not, in fact, be identical to the parent cell, but are still included within the scope of the term as used herein.

"Vector" or "construct" refers to a nucleic acid molecule into which a heterologous nucleic acid can be or is inserted. Some vectors can be introduced into a host cell allowing for replication of the vector or for expression of a protein that is encoded by the vector or construct. Vectors typically have selectable markers, for example, genes that encode proteins allowing for drug resistance, origins of replication sequences, and multiple cloning sites that allow for insertion of a heterologous sequence. Vectors are typically plasmid-based and are designated by a lower case "p" followed by a combination of letters and/or numbers. Starting plasmids disclosed herein are either commercially available, publicly available on an unrestricted basis, or can be constructed from available plasmids by application of procedures known in the art. Many plasmids and other cloning and expression vectors that can be used in accordance with the present invention are well-known and readily available to those of skill in the art. Moreover, those of skill can readily construct any number of other plasmids suitable for use in the invention. The properties, construction and use of such plasmids, as well as other vectors, in the present invention will be readily apparent to those of skill from the present disclosure.

The term "expression" as used herein refers to a multi-step process that includes transcription and translation of a gene and is often followed by folding, post-translational modification and targeting of the resulting protein. The amount of protein that a cell expresses depends on the tissue, the developmental stage of the organism and the metabolic or physiologic state of the cell.

"Sequence" means the linear order in which monomers occur in a polymer, for example, the order of amino acids in a polypeptide or the order of nucleotides in a polynucleotide.

"Sequence identity or similarity", as known in the art, is the relationship between two or more polypeptide sequences or two or more polynucleotide sequences, as determined by comparing the sequences. As used herein, "identity", in the context of the relationship between two or more nucleic acid sequences or two or more polypeptide sequences, refers to the percentage of nucleotide or amino acid residues, respectively, that are the same when the sequences are optimally aligned and analyzed. For the purposes of comparing a queried sequence against, for example, the amino acid sequence SEQ ID NO: 6, the queried sequence is optimally aligned with the human MAIL protein sequence, SEQ ID NO:1 and the best local alignment over the entire length of SEQ ID NO:1 (718 amino acids) is obtained.

Analysis can be carried out manually or using sequence comparison algorithms. For sequence comparison, typically one sequence acts as a reference sequence, to which a queried sequence is compared. When using a sequence comparison algorithm, test and reference sequences are input into a computer, sub-sequence coordinates are designated, if necessary, and sequence algorithm program parameters are designated.

Optimal alignment of sequences for comparison can be conducted, for example, by using the homology alignment algorithm of Needleman & Wunsch, J Mol. Biol., 48:443 (1970). Software for performing Needleman & Wunsch analyses is publicly available through the Institut Pasteur (France) Biological Software website: http://bioweb.pasteur.fr/seqanal/interfaces/needle.html. The NEEDLE program uses the Needleman-Wunsch global alignment algorithm to find the optimum alignment (including gaps) of two sequences when considering their entire length. The identity is calculated along with the percentage of identical matches between the two sequences over the reported aligned region, including any gaps in the length. Similarity scores are also provided wherein the similarity is calculated as the percentage of matches between the two sequences over the reported aligned region, including any gaps in the length. Standard comparisons utilize the EBLOSUM62 matrix for protein sequences and the EDNAFULL matrix for nucleotide sequences. The gap open penalty is the score taken away when a gap is created; the default setting using the gap open penalty is 10.0. For gap extension, a penalty is added to the standard gap penalty for each base or residue in the gap; the default setting is 0.5.

Hybridization can also be used as a test to indicate that two polynucleotides are substantially identical to each other. Polynucleotides that share a high degree of identity will hybridize to each other under stringent hybridization conditions. "Stringent hybridization conditions" has the meaning known in the art, as described in Sambrook et al., *Molecular Cloning: A Laboratory Manual*, Second Edition, Cold Spring Harbor Laboratory, Cold Spring Harbor, N.Y., (1989). An exemplary stringent hybridization condition comprises hybridization in 6× sodium chloride/sodium citrate (SSC) at about 45° C., followed by one or more washes in 0.2×SSC and 0.1% SDS at 50-65° C., depending upon the length over which the hybridizing polynucleotides share complementarity.

A "reporter gene" refers to a nucleic acid sequence that encodes a reporter gene product. As is known in the art, reporter gene products are typically easily detectable by standard methods. Exemplary suitable reporter genes include, but are not limited to, genes encoding luciferase (lux), β-galactosidase (lacZ), green fluorescent protein (GFP), chloramphenicol acetyltransferase (CAT), β-glucuronidase, neomycin phosphotransferase, and guanine xanthine phosphoribosyl-transferase proteins.

The term "marker" as used herein refers to a specific substance from a subject that has a particular molecular feature that makes it useful for measuring the progress of disease or the effects of treatment. Biological samples comprising the marker are taken at periodic intervals from the subject to measure the progress of disease or the effects of treatment. The first measure of the marker is compared to the second measure and/or subsequent measures. In another example, the measure of the marker can be compared to a reference, a standard or negative control.

A "marker" can be any naturally-occurring or polymer which can be detected, measured or monitored. For example, markers include, without limitation, sense and anti-sense strands of genomic DNA (i.e. including any introns occurring therein), RNA generated by transcription of genomic DNA (i.e. prior to splicing), RNA generated by splicing of RNA transcribed from genomic DNA, and proteins generated by translation of spliced RNA (i.e. including proteins both before and after cleavage of normally cleaved regions such as transmembrane signal sequences).

As used herein, "marker" can also include a cDNA made by reverse transcription of an RNA generated by transcription of genomic DNA (including spliced RNA). Markers can be inherited during reproduction. A marker can be an identifiable physical location on a chromosome (for example, a restriction enzyme cutting site,) whose inheritance can be monitored. Markers can be expressed regions of DNA or some segment of DNA with no known coding function but whose pattern of inheritance can be determined.

MAIL mRNA or MAIL proteins can be used as markers, which can be measured by employing conventional reverse transcription PCR techniques or the anti-MAIL antibodies herein described. Biological samples comprising MAIL mRNA or MAIL protein can be collected prior to starting treatment of a subject and thereafter at periodic intervals to measure the progress of disease or the effects of treatment. An increase in the level of MAIL mRNA or MAIL protein correlates to the progression of cancer while a decrease of MAIL mRNA transcription or MAIL protein translation indicates a regression of cancer. A relatively unchanged or stable level of MAIL mRNA or MAIL protein from one period to the next is indicative of little or no change in the state of the cancer.

The term "probe" refers to any molecule capable of selectively hybridizing or binding to a specifically intended target molecule, for example a marker of the invention. Probes can be either synthesized by one skilled in the art, or derived from appropriate biological preparations. For the purposes of detecting the target molecule, probes can be specifically designed to be labeled, as described herein. Examples of molecules that can be utilized as probes include, but are not limited to, RNA, DNA, proteins, antibodies, other organic polymers and organic monomers.

The terms "selectively hybridize" and "selectively bind" as used herein refers to the ability of a probe to bind to a particular or intended nucleic acid or polypeptide target sequence or molecule in a heterogeneous mixture of nucleic acids or polypeptides, for example a probe can selectively hybridize to a nucleotide sequence encoding a MAIL nucleotide or a MAIL polypeptide in a heterogeneous mixture.

The terms "reducing expression", "decreasing expression", "knocking down" and "knock down" as used herein refer to the reduction in the expression of one or more genes. This reduction in gene expression can be as a result of a reduction in the rates of transcription, translation or both. For example, MAIL gene expression can be reduced through the use of RNA interference technology. Suitable RNA interference techniques are described and reviewed by Sandy et. al in Biotechniques. 2005 August;39(2):215-24. Mammalian RNAi: a Practical Guide, which is incorporated by reference.

In one example of RNAi, small interfering RNAs (siRNA) are designed to hybridize to the mRNA that will be knocked down. RNA-degrading enzymes (RNAses) target the double-stranded RNA hybrid molecule, separate the two strands, and then proceed to destroy other single-stranded RNA molecules that are complementary to one of the segments. In the case of short hairpin RNA (shRNA) technology, a particular type of siRNA, RNAses detect double strands within a hair pin of the shRNA, and will also destroy all mRNAs that match the shRNA, thus preventing their translation and reducing expressing thereby lowering the activity of the gene.

This technology has reached clinical trials for the treatment of macular degeneration and RNAi has also been shown effective in the complete reversal of induced liver failure in murine models (Sirna Therapeutics, San Francisco, Calif.). Methods of treating disease using RNAi technology are further reviewed in Uprichard, The Therapeutic Potential of RNA Interference, FEBS Letters 2005 Aug. 19 and Barik, Silence of the Transcripts: RNA Interference in Medicine, Molecular Medicine 2005 Jul. 19, which are incorporated herein by reference. Methods of treating cancer using RNAi have also been described by Karagiannis and El-Osta in RNA Interference and Potential Therapeutic Applications of Short Interfering RNAs, Cancer Gene Therapy. 2005 May 13 and by Tan and Yin, Application of RNAi to Cancer Research and Therapy, Frontiers in Bioscience, 2005 May 1; 10: 1946-60 which are incorporated by reference.

Another technique which can be employed to knock down gene expression or reduce gene expression is the use of morpholino oligonucleotides. Morpholino oligonucleotides are molecules in antisense technology used to block access of other molecules to specific sequences within nucleic acid molecules. Morpholinos, usually 25 bases in length, bind to complementary sequences of RNA by standard nucleic acid base-pairing. Unlike many antisense structural types (e.g. phosphorothioates, siRNA), Morpholinos do not degrade their target RNA molecules. Instead, Morpholinos act by "steric blocking", binding to a target sequence within an RNA and simply getting in the way of molecules which might otherwise interact with the RNA Bound to the 5'-untranslated region of messenger RNA (mRNA), Morpholinos can interfere with progression of the ribosomal initiation complex from the 5' cap to the start codon. This prevents translation of the coding region of the targeted transcript which knocks down or reduces gene expression. This is useful experimentally when one wishes to know the function of a particular protein; Morpholinos provide a convenient means of knocking down expression of the protein and learning how that knockdown changes the cells or organism. Some Morpholinos knock down expression so effectively that after degradation of preexisting proteins the targeted proteins become undetectable by Western blot. Morpholino oligos were conceived by Dr. James E. Summerton (Gene Tools, LLC) and developed in collaboration with Dr. Dwight D. Weller (AVI BioPharma Inc.).

The term "antisense" as used herein refers to a noncoding molecule which is complementary to the bases of a coding sequence of mRNA. Introducing a transgene coding for antisense mRNA is another strategy used to reduce or knock down expression of a gene. A strand of antisense mRNA can also be introduced into the cytosol by microinjection.

Analogous molecules with modified backbones have been designed which change various characteristics of RNA, such as its instability to degradative enzymes, thermal stability and bond strength thereby altering gene expression. Some alternative antisense structural types include phosphorothioate, PNA (peptide nucleic acid), LNA (locked nucleic acid), and 2'-O alkyl oligos.

A "cancer-associated" body fluid is a fluid which, when in the body of a patient, contacts or passes through cancer cells or into which cells or proteins shed from cancer cells, are capable of passing. Exemplary cancer associated body fluids include blood fluids, lymph, ascites, gynecological fluids, cystic fluid, urine, saliva and fluids collected by peritoneal rinsing.

A "cancer" or "cancer cell" as used herein refers to any naturally occurring cell within a subject or sample that divides and reproduces abnormally with uncontrolled growth. Cancer cells include cell lines that are also created for the purposes of research, such as those transformed by viruses, oncogenic activation, as well as those isolated and immortalized from patients such as humans. Some cancer cell lines include but are not limited to MCF-7, MDA-MB231, MDA-MB (breast cancer lines), ovarian cancer line SKOV3, prostate cancer line PC3, lung cancer lines H322 and H838.

The terms "non-cancer cell" and "non-cancer sample" as used herein refer to a cell, or a plurality of cells lacking cancer.

A "dedifferentiated cell" as used herein refers to a specialized cell which has reverted towards to a simpler, more embryonic, unspecialized form that has the capacity to develop into every cell type in the human body, but not the extra-embryonic tissues such as the placenta and umbilical cord. Dedifferentiation can occur in the development of cancer.

The term "transformed cell" as used herein refers any cell in the patient that is malignant and includes cells in culture, such as those which have been transformed through the use of, radiation, chemical treatment, a virus, or other techniques known to immortalize cell lines. Transformed cell lines include and are not limited to U937, THP-1, HEK-293, 3T3 and all cancer cells.

The term "breast cancer" as used herein refers to all types of breast cancers including but not limited to non-metastatic and metastatic carcinomas, for example Infiltrating Ductal Carcinoma, Infiltrating Lobular Carcinoma, Medullary Carcinoma Mucinous (colloid) Carcinoma, Comedocarcinoma, Paget's Disease, Papillary Carcinoma, Tubular Carcinoma, Adenocarcinoma, NOS, Carcinoma, NOS, Intraductal Carcinoma, Lobular Carcinoma in situ (LCIS), Papillary Carcinoma, and Comedocarcinoma.

The "normal" level of expression of a marker, for example MAIL mRNA or MAIL protein, is the level of expression of the marker in cells of a patient, e.g. a human or a sample, not afflicted with cancer.

"Over-expression" and "under-expression" of a marker, for example MAIL mRNA or MAIL protein, refer to expression of the marker of a patient or a sample at a greater or lesser level, respectively, than normal level of expression of the marker (for example at least 1.25 fold greater or 0.5 fold lower).

Expression of a marker in a patient or sample is "significantly" higher or lower than the normal level of expression of a marker if the level of expression of the marker is greater or less, respectively, than the normal level by an amount greater than the standard error of the assay employed to assess expression, and preferably at least 1.25, 1.5, 1.75 and more preferably two, three, four, five or ten times that amount. Alternately, expression of the marker in the patient can be considered "significantly" higher or lower than the normal level of expression if the level of expression is at least about 1.25, 1.5, 1.75, two, and preferably at least about three, four, or five times, higher or lower, respectively, than the normal level of expression of the marker.

Cancer is "inhibited" if at least one symptom of the cancer is alleviated, terminated, slowed, or prevented. As used herein, cancer is also "inhibited" if recurrence or metastasis of the cancer is reduced, slowed, delayed, or prevented.

A kit is any manufacture (e.g. a package or container) comprising at least one reagent, for example, a probe, an antibody, or other material used for specifically detecting a marker of the invention, the manufacture being promoted, distributed, or sold as a unit for performing the methods of the present invention.

A "compound that increases the activity of a MAIL protein" includes any compound that results in an increase in IL-6 and/or MCP-1 and/or MCP-2 and/or IL-8 and/or IL-10 and/or GMCSF and/or GCSF and/or L-12p40 production and/or secretion. In one embodiment, such a compound can increase the expression of MAIL as determined at the RNA and/or protein level. In another embodiment, such a compound can increase the quantity of cell differentiation and/or maturation of surface antigens such as HLA-DR and/or CD11b and/or CD16. In another embodiment the compound can increase the rate or state of Histone 3 phosphorylation and/or acetylation.

A "compound that decreases the activity of a MAIL protein" includes any compound that results in decreased IL-6 and/or MCP-1 and/or MCP-2 and/or IL-8 and/or IL-1 and/or GMCSF and/or GCSF and/or L-12p40 production and/or secretion. In one embodiment, such a compound can decrease the rate of expression of MAIL as determined at the RNA and/or protein level. In another embodiment, such a compound can decrease the level of cell differentiation and/or maturation of surface antigens such as HLA-DR and/or CD11b and/or CD16. In another embodiment the compound can decrease the rate or state of Histone 3 phosphorylation and/or acetylation.

The term "high throughput" refers to an assay design that allows easy screening of multiple samples simultaneously and/or in rapid succession, and can include the capacity for robotic manipulation. Another desired feature of high throughput assays is an assay design that is optimized to reduce reagent usage, or minimize the number of manipulations in order to achieve the analysis desired. Examples of assay formats include 96-well or 384-well plates, levitating droplets, micro-array, macro-array and "lab on a chip" microenzyme chips used for liquid handling experiments. It is well known by those in the art that as miniaturization of plastic molds and liquid handling devices are advanced, or as improved assay devices are designed, greater numbers of samples can be processed using the design of the present invention.

The present invention relates to novel nucleic acids, polypeptides and proteins encoded by these nucleic acids, recombinant MAIL materials, antibodies, and methods involving the production, detection, and utilization of these materials.

In attempts to clone MAIL, a PCR-based strategy was employed. Oligonucleotide primers were synthesized according to the sequences set forth in SEQ ID NO: 14 and SEQ ID NO: 13. These primers were able to successfully amplify a portion of the MAIL sequence from position 1 to position 2157 of SEQ ID NO:2. In the present invention, the MAIL gene was cloned from genomic DNA. The MAIL gene was sequenced, and is shown as SEQ ID NO: 2.

Figure 3:
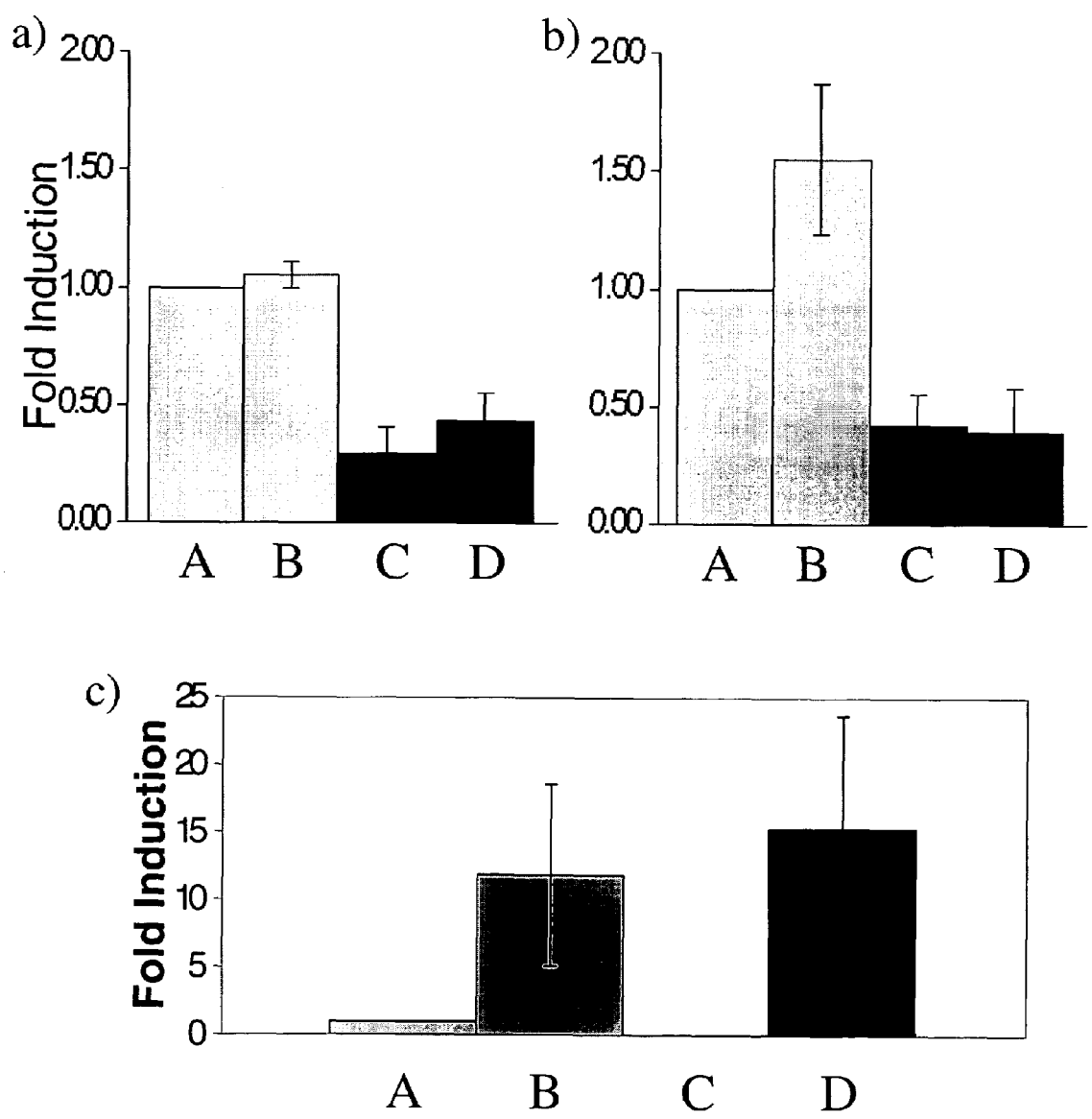
FIG. 3a, MAIL knock-down results in 50-75% downregulation of IL-8. Primary human monocytes were transfected with either vector alone (Sample A) or MAILpsil (Sample C), followed by LPS treatment for 4 hours (Sample B and Sample D respectively). Secreted IL-8 was measured using ELISA. In comparison with the control, IL-8 expression was reduced by 50-75% in MAILpsil transfected monocytes.
FIG. 3b, MAIL knock-down results in downregulation of MCP-1. Primary human monocytes were transfected with either vector alone (Sample A) or MAILpsil (Sample C), followed by LPS treatment for 4 hours (Sample B and Sample D respectively). Secreted MCP-1 was measured using ELISA. In comparison with the control, MCP-1 expression was reduced by 50-75% in MAILpsil transfected monocytes.
FIG. 3c, MAILpsil downregulates the basal expression of IL-12p40.

The invention also relates to isolated nucleic acid fragments. Isolated nucleic acids comprising fragments of SEQ ID NO:2 to SEQ ID NO:5 and SEQ ID NO:12 to SEQ ID NO:26 are useful for a variety of purposes. For example, these sequences can be used as oligonucleotide probes for the detection of MAIL nucleic acids or for the detection of sequences that flank MAIL nucleic acids. They can be used as oligonucleotide primers for the amplification of MAIL nucleic acids. For many methods, oligonucleotides of about 16-25 nucleotides, or from about 26-35 nucleotides in length are useful, although longer oligonucleotides of greater than about 35 nucleotides can also be utilized. Some oligonucleotides can be used as "primers" for the synthesis of complimentary nucleic acid strands. For example, DNA oligonucleotide primers can hybridize to a complimentary nucleic acid sequence to prime the synthesis of a complimentary DNA strand in reactions using DNA polymerases. Oligonucleotides are also useful for hybridization in several methods of nucleic acid detection, for example, in Northern blotting or in situ hybridization. Fluorescently-labeled oligonucleotides, for example, Cy3-dCTP-labeled fluorescent cDNA probes are particularly useful for use in hybridization methods using microarrays. Oligonucleotides can also be used for the preparation of chimeric nucleic acids that encode a portion or all of the MAIL polypeptide fused to another polypeptide sequence, for example, one or more motifs or domains of the MAIL sequence recombined with one or more motifs or domains from one or more heterologous sequences. In some embodiments this can affect the activity of the MAIL protein. Oligonucleotides can be used in other methods, for example, RT-PCR using SEQ ID:3 and SEQ ID:4 or SEQ ID: 12 to 15 can be used to identify MAIL, expression, over-expression and under-expression. Oligonucleotides such as SEQ ID: 19 can be used in techniques such as RNAi to reduce MAIL expression. Reducing MAIL expression would decrease the expression of cytokines and inflammatory cytokines, for example, IL-6, IL-8, L-12p40 and MCP-1. Examples of these methods are described infra in Example number 3 and FIGS. 2 and 3.

In addition to nucleic acid sequences encoding MAIL polypeptides, the invention also includes MAIL polypeptides, MAIL polypeptide variants, fragments of MAIL polypeptides and MAIL polypeptides having additional amino acids.

MAIL polypeptide variants are polypeptides capable of MAIL activity in which substitutions have been made in the amino acid sequence from the sequence shown in SEQ ID NO:1. These substitutions can be as a result of naturally occurring mutations during DNA synthesis, transcription or translation, the use of amino acid analogs, chemical modifications or other molecular biology techniques well known in the art.

Fragments of MAIL polypeptides include polypeptides capable of MAIL activity which are shorter in length than the sequence shown in SEQ ID NO:1. These fragments include any polypeptide capable of MAIL activity less than 718 amino acids in length. For example a fragment of MAIL can be from 60 to about 717 amino acids in length and still bind DNA. Fragments of MAIL polypeptides can be created by naturally occurring mutations during DNA synthesis, transcription or translation. Those skilled in the art will readily recognize that the use of enzymes which cleave either DNA or proteins, chemical modifications or other molecular biology techniques can be employed to create fragments of MAIL polypeptides.

MAIL polypeptides or MAIL polypeptide fragments can be generated using any sort of synthetic or molecular biological technique. Standard synthetic peptide techniques can be used to generate smaller MAIL polypeptide fragments, for example peptide fragments that are 500 amino acids in length or shorter. Techniques for the synthesis of peptides fragments are well known and are described in, for example, Barany and Merrifield, Solid-Phase Peptide Synthesis; pp. 3-284 in The Peptides: Analysis, Synthesis, Biology. Vol. 2: Special Methods in Peptide Synthesis, Part A., Merrifield, et al., Journal of the American Chemical Society, 85: 2149-2156 (1963), and Stewart et al., Solid Phase Peptide Synthesis, 2nd ed. Pierce Chem. Co., Rockford, Ill. (1984).

MAIL polypeptides having additional amino acids are also envisioned within the scope of the invention which are longer in length than the sequence shown in SEQ ID NO:1. As described herein, the MAIL polypeptide can also have additional amino acid residues at its amino terminus, its carboxyl terminus or both. Such additional residues are useful for a variety or purposes, including, for example, immunodetection, purification, cellular trafficking, enzymatic activity, protein modification etc. These proteins can include any polypeptide capable of MAIL activity which is greater than 718 amino acids in length. For example a recombinant MAIL can be from 719 amino acids to about 1500 amino acids in length and still be capable of MAIL activity. Recombinant MAIL polypeptides can be created by naturally occurring mutations during DNA synthesis, transcription or translation, the use of enzymes that ligate either DNA (such as T4 ligase) or fuse proteins.

A nucleic acid sequence can encode a MAIL fusion protein, which can include additional amino acid residues providing coordinates for bonding such as ionic, covalent, hydrogen or Van der Waals or combinations thereof with organic or inorganic compounds. Useful additional amino acid sequences include, for example, poly-histidine residues useful for protein purification via Ni+-coupled residue, constant domains of immunoglobulins (IgA, IgE, IgG, IgM) or portions thereof (CH1, CH2, CH3), albumin, hemagluttinin (HA) or myc affinity epitope tags useful for the formation of immuno-complexes for detection or purification (antibodies against these moieties can be obtained commercially), polypeptides useful for detection such as the green fluorescent protein (GFP), enzymes such as beta-galactosidase (B-Gal), Glutathione S transferase (GST), chloramphenicol acetyltransferase (CAT), luciferase, and alkaline phosphatase (A), signal sequences for protein trafficking and protease cleavage sequences useful for separating additional amino acid sequences from the MAIL sequence, if desired.

Those skilled in the art will readily recognize that chemical modifications or other molecular biology techniques can be employed to create recombinant proteins or protein fusions.

Fragments of MAIL and MAIL polypeptides having additional amino acids can comprise variant sequences in which substitutions have been made in the amino acid sequence as compared with the sequence shown in SEQ ID NO:2. These substitutions can be as a result of naturally occurring mutations during DNA synthesis, transcription or translation, the use of amino acid analogs, other molecular biology techniques, or chemical modifications well known in the art.

Due to the degeneracy of the genetic code, more than one codon can be used to encode a particular amino acid, and therefore, a MAIL amino acid sequence (for example, SEQ ID NO: 1) can be encoded by any one of a plurality of nucleic acid sequences. Isolated nucleic acid includes sequences wherein one or more codons in the sequence are replaced by codons of a different sequence but that code for the same amino acid residue are herein referred to as "conservative codon substitutions". Therefore, the invention encompasses nucleic acid sequences encoding SEQ ID NO:1 that have one or more than one conservative codon substitution. One of skill in the art would be able to determine a particular nucleic acid sequence having one or more than one conservative codon substitution and encoding SEQ ID NO: 2, based on the sequence information provided herein. Conservative codon substitutions can be made in the nucleic acid sequence encoding the MAIL polypeptide, for example, the codons TTT and TTC (collectively referred to as TTT/C) can encode a Phe (phenylalanine) residue; other codon substitutions are as follows: TTA/G and CTT/C/A/G: Leu; ATT/C: Ile; ATG: Met; GTT/C/A/G: Val; TCT/C/A/G: Ser; CCT/C/A/G: Pro; ACT/C/A/G: Thr; GCT/C/A/G: Ala; TAT/C: Tyr; CAT/C: His; CAA/G: Gln; AAT/C: Asn; AAA/G: Lys; GAT/C: Asp; GAA/G Glu; TGT/C: Cys; CGT/C/A/G: Arg; AGT/C: Ser; AGA/G; Arg; GGT/C/A/G:Gly. Conservative codon substitutions can be made at any position in the nucleic acid sequence that encodes the MAIL polypeptide.

Some residues share a common chemical property. Amino acids at positions 2 and 6 of SEQ ID NO:1 are hydrophobic amino residues, for example, isoleucine (I) or leucine (L). Other hydrophobic amino acids include glycine, valine, methioinine and proline. Other amino acid groups include "basic amino acids," which include histidine, lysine, and arginine; "acidic amino acids," which include glutamic acid and aspartic acid; "aromatic amino acids," which include phenylalanine, tryptophan, and tyrosine; "small amino acids," which include glycine and alanine; "nucleophilic amino acids," which include serine, threonine, and cysteine; and "amide amino acids," which include aparagine and glutamine. Amino acid substitutions can therefore be made in recombinant MAIL polypeptides while retaining the proteins's DNA binding activity, by selecting those amino acid which residues share a common chemical property at any given position. The invention also provides isolated nucleic acid molecules that are complementary to any isolated nucleic acid molecules, as described herein.

The isolated nucleic acids of the invention can also include nucleic acid sequences that encode the MAIL polypeptide having additional amino acid residues. In some embodiments, the additional amino acids are present at the amino terminus, the carboxyl terminus, within the MAIL sequence or combinations of these locations. MAIL polypeptides having these types of additional amino acid sequences can be referred to as "MAIL fusion proteins". In some cases, it may be more appropriate to refer to them otherwise as "chimeric" or "tagged" MAIL proteins, or the like, depending on the nature of the additional amino acid sequences. Nonetheless, one will be able to discern a MAIL polypeptide having additional amino acid sequences given the sequence information provided herein. The additional amino acid residues can be few in number, for example, from one to about 20 additional amino acid residues, or longer, for example, greater than about 20 additional amino acid residues. The additional amino acid residues can serve one or more functions or purposes including, for example, serving as epitopes for protein (e.g., antibody) or small molecule binding; serving as tags for intracellular and extracellular trafficking; providing additional enzymatic or other activity; or providing a detectable signal.

Recombinant techniques can be used for the expression of MAIL including but not limited to fragments of MAIL, variants of MAIL and fusions of MAIL with other proteins from host cells transformed with a MAIL nucleic acid. These methods include, for example, in vitro recombinant DNA techniques and in vivo genetic recombination (see, for example, the techniques described in Sambrook et al., Molecular Cloning, A Laboratory Manual, 3'd Edition, Cold Spring Harbor Press, NY (2001); and Ausubel et al., eds., Short Protocols in Molecular Biology, 4th Edition, John Wiley & Sons, Inc., NY (1999)).

MAIL can be produced by introducing an expression vector encoding a MAIL polypeptide into a cell and culturing the cells to express the polypeptide. When a purified MAIL polypeptide is desired, a step can also be performed to isolate and, if desired, purify the MAIL polypeptide.

In another embodiment, the invention provides a recombinant nucleic acid construct that includes the entire or a portion of the MAIL coding sequence operably linked to a regulatory sequence. These recombinant nucleic acid constructs include recombinant expression vectors suitable for expression of the MAIL nucleic acid in a host cell. Recombinant expression vectors include one or more regulatory sequences, which can be selected based on the type of host cells used for MAIL expression, operably linked to a MAIL nucleic acid sequence. Regulatory sequences include promoters, enhancers and other expression control elements, for example, poly (A)+ sequences. Regulatory sequences can be specific for prokaryotic cells, for example, bacterial cells, such as E. coli, or for eukaryotic cells, such as yeast cells, insect cells or mammalian cells (for example, HEK293, U937, THP-1, HEK, CHO or COS cells). Regulatory sequences can be located cis or trans relative to the MAIL nucleic acid sequence. Regulatory sequences can include constitutive expression sequences that typically drive expression of the nucleic acid under a wide variety of growth conditions and in a wide variety of host cells, tissue-specific regulatory sequences that drive expression in particular host cells or tissues and inducible regulatory sequences that drive expression in response to a secondary factor. Choice and design of the expression vector can depend on such factors as the particular host cell utilized and the desired levels of polypeptide expression. Other expression vector components can include, but are not limited to, one or more of the following: a signal sequence, an origin of replication, one or more genes that facilitate selection of a transformed cell or nucleic acid from the transformed cell and a transcription termination sequence. Genes facilitating selection of transformed cells encode proteins that (a) confer resistance to antibiotics or other toxins, for example, ampicillin, neomycin, methotrexate or tetracycline, (b) complement auxotrophic deficiencies or (c) supply critical nutrients not available from complex media.

Recombinant nucleic acid constructs used for expression of the MAIL polypeptide can also include constructs that can be transcribed and translated in vitro, for example, constructs having a T7 promoter regulatory sequence.

Vectors suitable for the expression of MAIL are known in the art and commercially available. Suitable vectors include, for example, pET-14b, pcDNAlAmp and pVL1392, which are available from Novagen and Invitrogen and can be used for expression in E. coli, COS cells and baculovirus infected insect cells, respectively.

In another embodiment, the invention provides a recombinant cell that includes a MAIL nucleic acid. Recombinant cells include those wherein a nucleic acid sequence has been introduced. Typically, recombinant cells are created by introducing a particular nucleic acid into cells using molecular biological techniques. However, recombinant cells also include cells that have been manipulated in other ways to promote the expression of a desired nucleic acid sequence. For example, regions that are proximal to a target nucleic acid sequence can be altered to promote expression of the target nucleic acid, or genes that act to regulate the expression of a target nucleic acid can be introduced into a cell.

Recombinant cells, after periods of growth and division, may not be identical to the starting parent cell; however, these cells are still referred to as recombinant cells and are included within the scope of the term as used herein.

Host cells suitable for harboring and providing the machinery for MAIL expression include any prokaryotic or eukaryotic cells. Examples of suitable prokaryotic host cells are eubacteria, such as Gram-negative or Gram-positive organisms, for example, Enterobacteriaceae such as *Escherichia*, for example, *E. coli, Enterobacter, Salmonella*, for example, *Salmonella typhimurium*, as well as Bacilli such as *B. subtilis, Pseudomonas*, and *Streptomyces*. Many higher eukaryotic host cells can be used, including insect cells, such as *Drosophila* S2 and *Spodoptera* Sf9 cells, mammalian cells, such as U937, THP-1, Chinese Hampster Ovary (CHO) cells, monkey kidney (COS) cells, canine kidney (MDCK) cells, human cervical carcinoma (HeLa) cells, and human embryonic kidney (HEK) cells as well as plant cells.

Growth of the transformed host cells can occur under conditions that are known in the art. The conditions will generally depend upon the host cell and the type of vector used. Suitable induction conditions, such as temperature and chemicals, can be used and will depend on the type of promoter utilized. Examples of suitable media for the propagation of prokaryotes include LB, Luria broth (LB), also known as Miller's L Broth. Examples of suitable media for the propagation of eukaryotes include, Minimal Essential Medium (MEM), RPMI-1640 and Dulbecco's Modified Eagle's Medium (DMEM). As shown Example, human monocytes were isolated were isolated and cultured in RPMI 1640 supplemented with 10% fetal bovine serum and L-glutamine and incubated at 37° C., with 5% $CO^2$.

Nucleic acids, including expression constructs, can be introduced into prokaryotic or eukaryotic cells via conventional transformation or transfection techniques. As used herein, the terms "transformation" and "transfection" are intended to refer to a variety of art-recognized techniques for introducing a foreign nucleic acid molecule (e.g., DNA) into a host cell, including calcium phosphate or calcium chloride co-precipitation, DEAE-dextran-mediated transfection, lipofection, virus mediated introduction, biolistics or electroporation. Suitable methods for transforming or transfecting host cells can be found in Sambrook, et al. (supra), and other laboratory manuals.

Recombinant cells can be useful for the production of a MAIL polypeptide for purification purposes or for functional studies involving the MAIL polypeptide. For example, a recombinant MAIL cell can be used to test a number of compounds for their ability to alter the activity of the MAIL polypeptide. The recombinant MAIL cell can also be used to test how altering various properties of the MAIL polypeptide, for example, altering the amino acid sequence of the MAIL polypeptide, affects MAIL activity.

Figure 5:
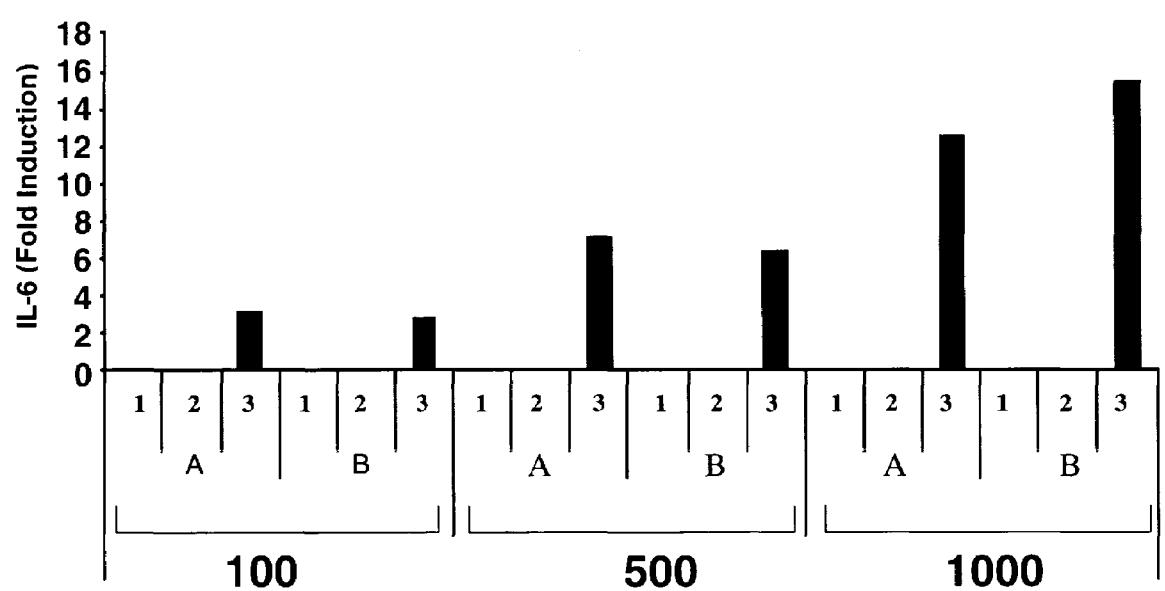
FIG. 5, Over-expression of MAIL, in HEK293 cells using MAILAdC20 increases IL-6 secretion. HEK293 cells were transduced with an AdC20 control virus or a MAIL adenovirus at MOI of 100 virons/cell, 500 virons/cell, or 1000 virons/cell. Culture supernatants from untransduced (Sample 1), empty-vector transduced (Sample 2) or MAIL over-expressing (Sample 3) HEK293 were harvested and analyzed for IL-6 secretion using ELISA. Comparable levels of IL-6 induction was observed between untreated cells (Set A) and cells stimulated with LPS (1 µg/ml) for 4 hours (Set B).
Figure 6:
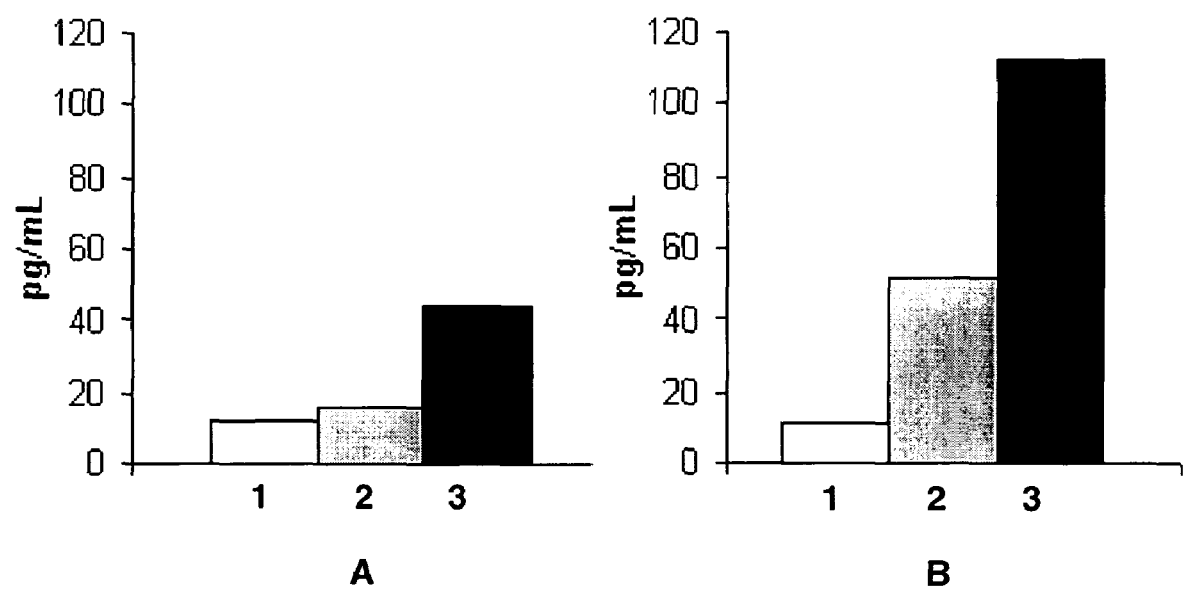
FIG. 6, LPS induced IL-6 and IL-10 levels are elevated in MAIL-THP-1 cells. Untransduced THP-1 (Sample 1), Lenti-DsRED-THP-1 (Sample 2) and MAIL-THP-1 (Sample 3) cells were treated with 1 µg/ml LPS for 24 hours. Culture supernatants were analyzed for IL-6 (Set A) and IL-10 (Set B) secretion. Both cytokines were found to be elevated in LPS treated MAIL-THP1 cells.
Figure 7A:
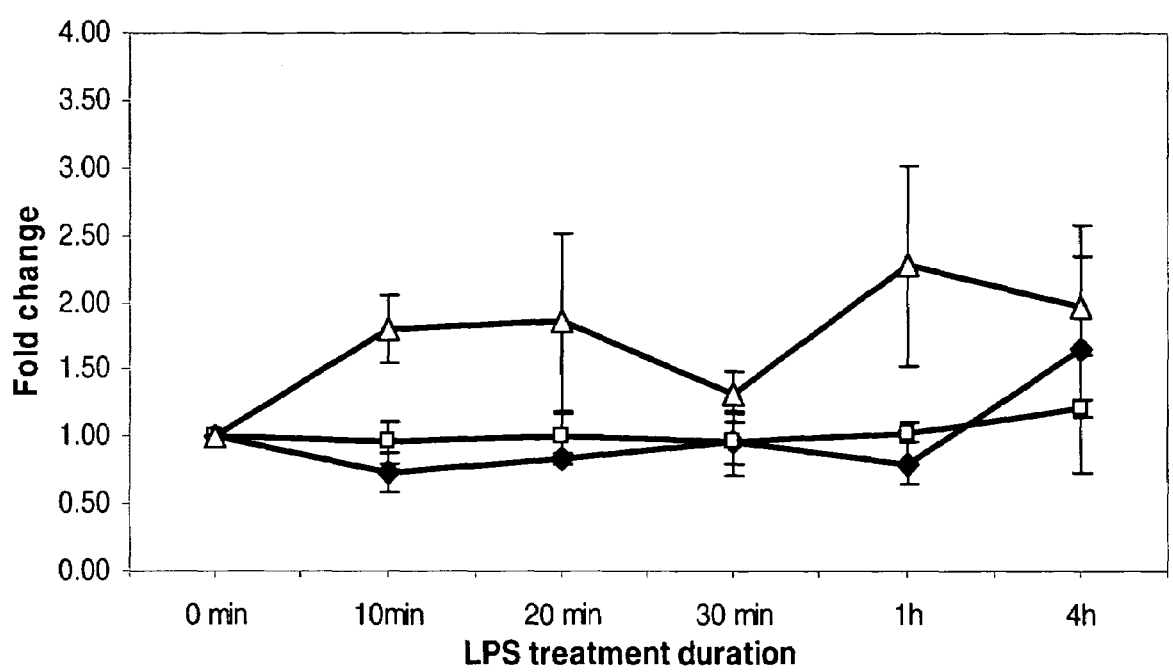
FIG. 7a, MAIL over-expression increases global levels of H3 phosphorylation (Ser 10). Untransduced (Diamond line), Control-THP-1 (Square line), or MAIL-THP-1 (Triangle line) were treated with LPS (1 µg/ml) for 0 minutes, 10 minutes, 20 minutes, 30 minutes, 1 hour, or 4 hours respectively. Cell lysates were sequentially analyzed by western blotting using anti-phospho-Histone H3 (Ser 10) and anti-GAPDH antibodies. Modification versus GAPDH signals were quantitated using the Lumimager.
Figure 7B:
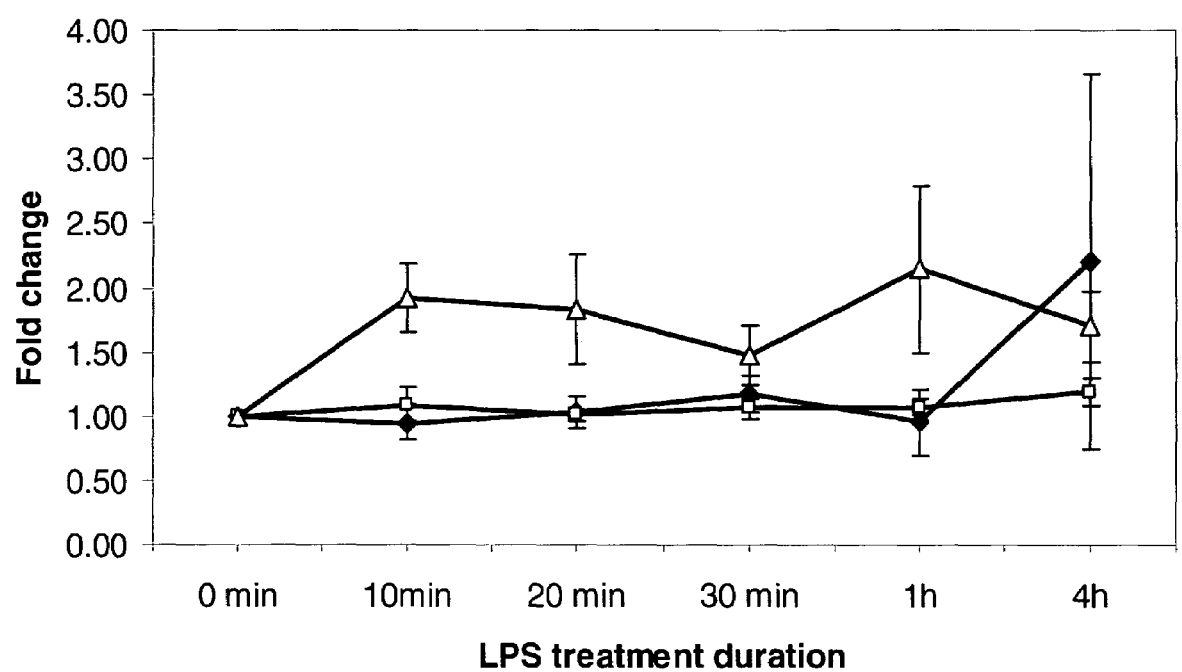
FIG. 7b, MAIL, over-expression increases global levels of H3 acetylation (Lys 14). Untransduced (Diamond line), Lenti-puro control transduced (Square line), or MAIL-THP-1 (Triangle line) were treated with LPS (1 µg/ml) for 0 minutes, 10 minutes, 20 minutes, 30 minutes, 1 hour, or 4 hours respectively. Cell lysates were sequentially analyzed by western blotting using anti-acetyl-Histone H3 (Lys 14) and anti-GAPDH. Modification versus GAPDH signals were quantitated using the Lumimager.

In one embodiment, THP-1 cells that can over-express MAIL have been generated, using a lentiviral vector, plenti-MAIL-puro, see Example 6 and FIGS. 6 and 7. It has now been shown that MAIL over-expressing THP-1 cells produce higher levels of IL-6 upon LPS stimulation in comparison to normal THP-1 cells, see FIGS. 6 and 7. In some embodiments primary human monocytes can also be transduced with the vector, plenti-MAIL-puro resulting in increased IL-6 production, and can be used in high throughput screens. In another embodiment, an adenoviral vector can be used to over-express MAIL in HEK293 cells, resulting in IL-6 production, see Examples 2, 6 and FIG. 5. In a further embodiment this system can also be used in high throughput screening applications, see Example 8. In other embodiments, a recombinant MAIL protein was generated (either untagged, 6xHis or GST tagged) from either Sf9 cells, E. coli or from cell lines including HEK293.

A variety of methods can be used for the purification of the MAIL polypeptide. For example, crude purification can be performed using ammonium sulfate precipitation, centrifugation or other known techniques. A higher degree of purification can be achieved by suitable chromatographic techniques, including, for example, anion exchange, cation exchange, high performance liquid chromatography (HPLC), gel filtration, hydrophobic interaction chromatography and affinity chromatography, for example, immunoaffinity chromatography using antibodies directed against the MAIL protein. If needed, steps for refolding the MAIL proteins can be used to obtain the active conformation of the protein when the protein is denatured during intracellular synthesis, isolation or purification such as resuspending the protein in 6M urea and dialyzing out the urea to facilitate protein refolding.

The antibodies and constructs used to knock-in or knock-out MAIL can be used to identify dedifferentiated cells in which MAIL expression is altered and various cancers in which MAIL expression is altered. It has now been demonstrated that the expression of MAIL is higher in metastatic breast cancer, colon cancer, osteosarcoma, gastro stromal tumor, ovarian cancer, urinary bladder, liver cancer, stomach cancer, mesothelioma, gastric, esophagus, cervical and rectal cancer, pancreatic cancer, endometrical cancer, prostate cancer, esophagal cancer, thyroid cancer, skin squamous cell cancer, neuroblastoma, nerve sheath malignant tumor, lung cancer, colon cancer, skin basal cell cancer, T cell lymphomas, synovial sarcoma, seminoma, rhabdomyosarcoma, Leiomyosarcoma, kidney cancer, fibrosarcoma and Ewings sarcoma, glioma, ovarian yolk sac tumor (endodermal sinus tumor), melanoma, medulloblastoma, Hodgkin's disease and B cell lymphoma tissue, than in normal tissue. Although IL-6 expression is higher in breast cancer in comparison to normal tissue, a significant difference between benign and malignant tissue was not demonstrated by IHC (data not shown). Analysis of MAIL expression therefore provides an excellent marker for prediction of metastatic potential in breast cancer as well as other cancers, especially in cancers where IL-6, IL-8 and IL-10 are linked to cancer pathology.

The present invention is based, in part, on the identification of a novel marker, MAIL which is over-expressed in cancer cells as compared to expression in normal (i.e. non-cancerous) cells. The markers of the invention correspond to DNA, RNA, antibodies and polypeptide molecules which can be detected in many different types of cells and tissues. The increased expression of one or more of these markers in cells has herein been correlated with the cancerous state of the tissue. The invention therefore includes compositions, kits, and methods for assessing the cancerous state of cells (for example cells obtained from a human, cultured human cells, archived or preserved human cells, in vivo cells and other samples).

The invention also provides novel antibodies that selectively bind to the proteins of the present invention as well as fragments thereof. Such antibodies can be used to quantitatively or qualitatively detect the protein or peptide molecules of the present invention. As used herein, an antibody selectively binds a target protein or polypeptide fragment when an antibody binds the protein or polypeptide fragment and does not significantly bind to non-target proteins, i.e., the antibody does not bind non-MAIL related polypeptides or proteins.

As used herein, an antibody is defined in terms consistent with that recognized within the art: antibodies are multi-subunit proteins produced by any vertebrate organism in response to an antigen challenge. The antibodies of the present invention include monoclonal antibodies and polyclonal antibodies, as well as fragments of such antibodies, including, but not limited to, Fab or F(ab')hd 2, Fc, and Fv fragments. Many methods are known for generating and/or identifying antibodies to a given target peptide. Several such methods are described by Harlow, Antibodies, Cold Spring Harbor Press, (1989). In general, to generate antibodies, an isolated peptide is used as an immunogen and is administered to a mammalian organism, such as a rat, rabbit or mouse. Either the full-length protein, an antigenic peptide fragment, or a fusion protein can be used.

Monoclonal antibodies can be produced by hybridomas, which are immortalized cell lines capable of secreting a specific monoclonal antibody. The immortalized cell lines can be created in vitro by fusing two different cell types, usually lymphocytes, one of which is a tumor cell.

Antibodies can be prepared from regions or discrete fragments of the protein containing the desired amino acid sequence. Antibodies can be prepared from any region of the peptide as described herein. However, regions which include those involved in function/activity and/or protein/binding partner interaction are preferred. An antigenic fragment will typically comprise at least 10 contiguous amino acid residues. The antigenic peptide can comprise, however, at least 12, 14, 20 or more amino acid residues. Such fragments can be selected on a physical property, such as fragments corresponding to regions that are located on the surface of the protein, e.g., hydrophilic regions or can be selected based on sequence uniqueness, or based on the position of particular amino acid residue(s) or amino acid residue variants of the polypeptides provided by the present invention.

Detection of an antibody of the present invention can be facilitated by coupling (i.e., physically linking) the antibody to a detectable substance. Examples of detectable substances include various enzymes, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

Immunoprecipitation of MAIL using the antibodies of the present invention for detection of proteins interacting with MAIL is also envisioned within the scope of the present invention. Immunoprecipitation can also be used for example to discover new disease targets. The MAIL antibody can be linked to any immobilizing surface, such as Protein G-sepharose or Protein A-sepharose for the purpose of MAIL purification, to identify interacting proteins and potential drug targets. Additionally, the process can be used to determine the molecular weight and isoelectric point of immunoprecipitated proteins by one-dimensional or two-dimensional SDS-PAGE or LC MS/MS. Immunoprecipitation can be used to verify that an antigen of interest is synthesized by a specific tissue (i.e., that a labeled protein can be identified in tissues or cells cultured with labeled precursors). This procedure can be used to determine whether a protein contains carbohydrate residues by evaluating whether immunoprecipitated antigen from cells cultured with labeled monosaccharides is labeled. Characterization of the type of covalent modification, such as phosphorylation or glycosylation wherein the carbohydrates present on glycoproteins, can be performed by evaluating the incorporation of different labeled monosaccharides into immunoprecipitated proteins during cell culture and testing whether inhibitors of glycosylation alter the molecular weight of the immunoprecipitated protein. Immunoprecipitation can be used to determine precursor-product relationships by performing pulse-chase labeling followed by immunoprecipitation. Immunoprecipitation can be used to quantify synthesis rates of proteins in culture by determining the quantity of immunoprecipitated, labeled protein. Methods and reagents for immunoprecipitation are well known in the art and can be obtained from eBioscience, San Diego, Calif. or Upstate USA, Inc. Charlottesville, Va.

Immunohistochemistry using anti-MAIL antibodies was performed to screen breast cancer tissues and can be used in predicting metastatic potential, in combination with MAIL as a marker. In another aspect of the invention, immunohistochemistry using anti-MAIL antibodies can be performed to screen tissues of any type for the presence of cancer and can be used in predicting metastatic potential, in combination with MAIL as a marker.

The invention includes, antibodies useful for immunohistochemistry (IHC) and western blotting applications, for example, human MAIL specific antibodies against six different regions within the human MAIL protein. For example, three peptides of the present invention were synthesized ("M1," SEQ ID NO:6, "M2," SEQ ID NO:7, "M3" SEQ ID NO:8), coupled to KLH and used to immunize rabbits respectively. Polyclonal anti-MAIL antisera, against M1, M2 and M3 were collected, pooled and tested for specificity against purified MAIL protein by western blotting. In another example, the polyclonal anti-MAIL antiserum, M456 can be obtained by immunizing a rabbit with a pool of three KLH coupled antigenic peptides ("M5," SEQ ID NO:9, "M6," SEQ ID NO:10, "M7" SEQ ID NO:11).

M1, M2, M3 and M456 anti-human MAIL antibodies are the only antibodies known against human MAIL and have been successfully utilized by the applicants for western blotting and immunohistochemistry (IHC). Immunohistochemistry of the present invention shows that the expression of MAIL is higher in metastatic breast cancer tissue in comparison to normal or benign tissues.

As shown infra, MAIL expression in normal, benign, and malignant breast cancer tissue can be by IHC using the antibodies of the present invention and compared to a pre-immune control staining of malignant tissue. For example, normal, benign and malignant breast cancer tissue sections can be analyzed for MAIL expression and IL-6 expression using immunohistochemistry as shown in Example 7. MAIL immunolabeling was seen as brown staining. In some methods tissues can be graded by the intensity of the brown staining in the breast epithelial/tumor cells (scores: 0=no detectable staining; 1=weak, light brown staining; 2=moderate, brown staining; 3=strong, dark brown staining). All scores can then be averaged per group and plotted. Weak MAIL immunolabeling is detected in normal and benign tissues, while more intense MAIL immunolabeling is detected in the malignant breast cells.

In another example, MAIL expression in multiple malignant cancer tissues can be examined by IHC using the antibodies of the present invention and compared to a pre-immune control staining. No staining is observed when the antibodies are pre-incubated with the antigenic peptide pool prior to probing.

Very weak MAIL immunolabeling was detected in T cell lymphomas, synovial sarcoma, seminoma, rhabdomyosarcoma, Leiomyosarcoma, kidney cancer, fibrosarcoma and Ewings sarcoma, glioma, ovarian yolk sac tumor (endodermal sinus tumor), melanoma, medulloblastoma, Hodgkin's disease and B cell lymphoma (score=1). Weak to moderate staining was observed in pancreatic cancer, endometrical cancer, prostate cancer, esophagus cancer, thyroid cancer, skin squamous cell cancer, neuroblastoma, nerve sheath malignant tumor, lung cancer, colon cancer, skin basal cell cancer (score range 1.15 to 1.5); urinary bladder, liver cancer, stomach cancer, mesothelioma, gastric, esophagus, cervical and rectal and ovarian cancer (score range 1.7 to 2.05), while more intense MAIL immunolabeling was detected in colon cancer, osteosarcoma, gastro stromal tumor and breast cancer (score range 2.4 to 3). As discussed infra in Example 7, these data suggest an up-regulation of MAIL is associated with various cancer pathologies.

In other examples MAIL antibodies can be used to detect a dedifferentiated cell in a tissue sample. For example a tissue sample can be contacted with at least one antibody that selectively binds to a polypeptide such as: SEQ ID NO: 6; SEQ ID NO: 7; SEQ ID NO: 8; SEQ ID NO: 9; SEQ ID NO: 10; or SEQ ID NO: 11. Next any conventional technique know in the art, such as IHC, immunoprecipitation, ELISA, antibodies conjugated to magnetic beads or FACS, can be used to detect the binding of the antibody in the sample. Increased levels of antibody binding in the tissue sample relative to a non-cancer control indicates at least one dedifferentiated cell in a tissue sample.

The invention additionally includes methods for the detection of cancer wherein antibodies against major histocompatibility complex (MHC) class I molecules and/or antibodies against major histocompatibility complex (MHC) class II molecules can be employed in combination with antibodies against MAIL. The novel combination of an antibody against an MHC marker with a MAIL antibody can be used to detect various types of cancers such as those disclosed, supra.

Studies have shown a decrease in the expression MHC class I and/or and increase in the expression of MHC class II molecules in cervical intraepithelial neoplasia (CIN) and in cervical cancers (Sikorski, M. et al., Dynamics of selected MHC class I and II molecule expression in the course of HPV positive CIN treatment with the use of human recombinant IFN-γ. Acta Obstetricia et Gynecologica Scandinavica 2004 March;83(3):299-307). Therefore, the expression of MHC molecules can be monitored as markers of cancer in combination with the expression of MAIL markers.

In the present invention MHC class I and MHC class II molecules can be employed as markers, wherein the level of expression of the markers in a patient sample is compared to the level of expression in a control non-cancer sample. Changes in the expression of MHC class I and MHC class II molecules can be used as markers in multiple malignant cancer tissues and can be examined by techniques well known in the art such as, RT-PCR, IHC, immunoprecipitation, antibody conjugated to magnetic beads, or FACS.

MAIL expression in a patient sample is compared to the level of expression in a control non-cancer sample. At least a two-fold elevated expression of the MAIL marker and a decrease in the expression of at least one MHC class I marker in the patient sample indicates cancer. Furthermore, at least a two-fold elevated expression of the MAIL marker and an increase in the expression of at least one MHC class II marker in the patient sample indicates cancer.

MHC and MAIL markers can be assayed, measured or monitored at the same time period, or MHC and MAIL markers can be analyzed at different time periods, in different experiments and the data can be compared at any desired time point.

Suitable MHC class I molecules that can be used as markers, include but are not limited to HLA-A, HLA-B and HLA-C. Additionally, suitable MHC class II molecules that can be used as markers include but are not limited to HLA-DR, HLA-DQ and HLA-DP. Those skilled in the art will appreciate that antibodies can be created against virtually any epitope within the MHC class I and MHC class II molecules so that the antibody can be employed in the methods and kits of the present invention.

In practicing the present invention, many conventional techniques in molecular biology, microbiology and recombinant DNA are used. These techniques are well-known and are explained in, for example, Current Protocols in Molecular Biology, Vols. I, II, and III, F. M. Ausubel, ed. (1997); and Sambrook et al., Molecular Cloning: A Laboratory Manual, Cold Spring Harbor Laboratory Press, Cold Spring Harbor, N.Y. (2001). The compositions, kits, and methods of the invention have the following uses, among others: 1) assessing whether a patient is afflicted with cancer; 2) assessing the stage of cancer in a human patient; 3) monitoring the progression of cancer in a patient; 4) selecting a composition or therapy for inhibiting cancer in a patient; 5) assessing the efficacy of one or more test compounds for inhibiting cancer in a patient; 6) assessing the efficacy of a therapy for inhibiting cancer in a patient; 7) treating a patient afflicted with cancer; 8) inhibiting cancer in a patient; 9) assessing the carcinogenic potential of a test compound; and 10) inhibiting cancer in a patient at risk for developing cancer.

The invention thus includes a method of assessing whether a patient is afflicted with cancer such as; breast cancer, colon cancer, osteosarcoma, gastro stromal tumor, ovarian cancer, urinary bladder, liver cancer, stomach cancer, mesothelioma, gastric, esophagus, cervical and rectal cancer, pancreatic cancer, endometrial cancer, prostate cancer, esophagal cancer, thyroid cancer, skin squamous cell cancer, neuroblastoma, nerve sheath malignant tumor, lung cancer, colon cancer, skin basal cell cancer, T cell lymphomas, synovial sarcoma, seminoma, rhabdomyosarcoma, Leiomyosarcoma, kidney cancer, fibrosarcoma and Ewings sarcoma, glioma, ovarian yolk sac tumor (endodermal sinus tumor), melanoma, medulloblastoma, Hodgkin's disease and B cell lymphoma.

This method comprises comparing the level of expression of the marker, MAIL in a patient sample and the normal level of expression of the marker in a control, e.g., a non-cancer sample, either from the patient's own non cancerous tissue or another individual. A significant increase in the level of expression of the marker in the patient sample compared to the normal level is an indication that the patient is afflicted with cancer. The marker can be selected from any MAIL RNA, DNA, proteins, antibodies or other MAIL polymers.

The invention also further includes a method of assessing the stage of cancer in a patient. MAIL can be used as a marker to compare clinically diagnosed tumor tissues and any adjacent tissue at the mRNA level by RT-PCR or at the protein level using the antibodies described herein to identify potentially cancerous tissues and determine if cancer is spreading or if there has been metastasis. RT-PCR or IHC, ELISA, western blotting or immunoprecipitation can be employed to identify tissue which is potentially cancerous. Samples or biopsies of the tissues can be collected from a patient. The diagnosed tumor tissue contains a level of the marker, MAIL which can be compared to the adjacent tissue levels of MAIL mRNA or MAIL protein and compared. The biopsies and tissue comparisons will be repeated at regular intervals as determined by one skilled in the art to monitor the stage of the disease, progression of cancer into adjacent tissues or the response of the patient to treatment.

Any marker or combination of markers, as well as any known markers in combination with the markers set forth in, SEQ ID NO:3 through SEQ ID NO:11, and markers selected from MAIL RNA, MAIL DNA (for example SEQ ID NO:2), MAIL protein (for example SEQ ID NO:1), MAIL antibodies or other MAIL polymers can be used in the compositions, kits, and methods of the present invention. In general, it is preferable to use markers for which the difference between the level of expression of the marker in cancer cells and the level of expression of the same marker in normal non-cancerous cells is as great as possible. Although this difference can be as small as the limit of detection of the method for assessing expression of the marker, it is preferred that the difference be at least greater than the standard error of the assessment method, and preferably a difference of at least 1.25, 1.5, 1.75, 2, 3, 4, 5, 6, 7, 8, 9, 10, 15, 20, 25, 100, fold or greater.

It is recognized that certain markers are proteins which are secreted from cells (i.e. one or both of normal and cancerous cells) to the extracellular space surrounding the cells. These markers are preferably used in certain methods, embodiments, compositions, and kits of the invention, and each of these markers can be detected in a cell-associated body fluid sample, which can be more easily collected from a human patient than a tissue biopsy sample. In addition, preferred in vivo techniques for detection of a protein corresponding to a marker of the invention include introducing into a subject a labeled antibody directed against the protein. For example, the antibody can be labeled with a radioactive marker whose presence and location in a subject can be detected by standard imaging techniques.

In some embodiments of the compositions, kits, and methods of the invention, intracellular proteins such as cytoplasmic proteins and nuclear proteins can be employed. Mail proteins have been identified in the cytoplasm and the nucleus. Therefore, in other techniques of this invention, methods are used to access MAIL proteins in the cell interior, including the nucleus. Some of these techniques require disruption of the cell membrane can be accomplished through the use of mechanical shearing, sonication, enzymatic digestion or the use of buffers such as RIPA buffer as shown in Examples 2 and 6.

One skilled in the art can determine whether any particular marker corresponds to a secreted protein, membrane bound, cytoplasmic or nuclear protein. In order to make this determination, the protein corresponding to a marker is expressed in a test cell (e.g. a cell of an characterized cell line), extracellular fluid, a membrane fraction, a cytoplasmic fraction or a nuclear fraction of a cell sample is collected, and the presence or absence of the protein in the extracted fluid is assessed (e.g. using an antibody or a labeled antibody which binds specifically with the protein). Since MAIL is over expressed in cancer, the MAIL protein and/or MAIL mRNA can serve as a target in treatment of the cancers disclosed herein. The present invention demonstrates the function of MAIL in the regulation of inflammatory responses in primary human monocytes. As demonstrated in the examples, MAIL regulates the basal and the LPS induced expression of the pro-inflammatory cytokines IL-6, IL-8 and the chemokine MCP-1. Therefore, controlling MAIL levels can alter the course of a cancer.

Further to this strategy, the present invention shows that MAIL knock-in and knock-down/reducing expression affects the expression of various inflammatory cytokines and chemokines such as IL-6, IL-8, IL-12p40, MCP-1, MCP-2 as well as IL-10 in primary human monocytes as well as the promonocytic cell line THP-1. The present invention enables the regulation of inflammatory cytokines and chemokines by modulating MAIL expression. These cytokines play key roles in chronic inflammatory diseases such as inflammation, autoimmune diseases such as systemic Lupus Erythematosus, Rheumatoid arthritis, Alzheimer's disease, myocardial infarction, multiple sclerosis, Crohn's disease, transplant rejection, Paget's disease, osteoporosis, and various hyperproliferative disorders such as solid tumors such as renal cell carcinoma, breast, prostate and bladder cancers, certain neurological cancers, B cell malignancies, psoriasis, allergic contact dermatitis and other atopic eczemas, chronic inflammatory bowel disease (Trikha 2003, Asadullah et al. 2003). In addition it has been shown that there is a molecular link between inflammation and cancer (Florian R. G. et al., IKKβ Links Inflammation and Tumorigenesis in a Mouse Model of Colitis-Associated Cancer., Cell, Volume 118, Issue 3, Pages 271-401, 6 Aug. 2004). This study demonstrated that inactivation of I-kappa-B kinase (IKK beta), a pro-inflammatory gene, acts differently in two cell types to cause cancer. These data demonstrate that MAIL, which also is involved in regulation inflammation is a suitable target for the treatment of the aforementioned diseases and in addition, a target for the treatment of cancer.

Therefore, in another general aspect, the present invention relates to the use of MAIL nucleic acids and proteins in selecting a composition or therapy for inhibiting cancer in a patient and methods for identifying therapeutic compounds, for example, compounds useful in treating cancer. These types of compounds can be identified using a system that includes a MAIL polypeptide or a MAIL nucleic acid. Compounds can be tested directly in vivo, for example, in a rat, mouse, canine, or monkey model system or directly in bacterial cultures or in eukaryotic cell cultures. Particularly useful systems also include animal models of cancer, such as nude mice and cancer cell lines MDA-MB231, MDA-MB435, MCF-7, SKOV3, CAOV3, PC3, HCT-119, HT-29. These methods comprise assaying for the ability of various compounds to increase or decrease the expression of the MAIL protein or the activity of the MAIL protein as shown in Example 8. The compound screening and identification methods can be performed using conventional laboratory formats or in assays adapted for high throughput.

Candidate compounds encompass numerous chemical classes, including but not limited to, small organic or inorganic compounds, natural or synthetic molecules, such as antibodies, proteins or fragments thereof, antisense nucleotides, interfering RNA (iRNA) and ribozymes. Preferably, the candidate compounds are small organic compounds, i.e., those having a molecular weight of more than 100 Daltons yet less than about 1000 Daltons. Candidate compounds comprise functional chemical groups necessary for structural interactions with polypeptides, and can include at least an amine, carbonyl, hydroxyl or carboxyl group, two of the functional chemical groups or three or more of the functional chemical groups. The candidate compounds can comprise cyclic carbon or heterocyclic structure and/or aromatic or polyaromatic structures substituted with one or more of the above-identified functional groups. Candidate compounds also can be biomolecules such as peptides, saccharides, fatty acids, sterols, isoprenoids, purines, pyrimidines, derivatives or structural analogs of the above, or combinations thereof and the like. Where the compound is a nucleic acid, the compound typically is a DNA or RNA molecule, although modified nucleic acids having non-natural bonds or subunits are also contemplated. Modified nucleic acids can comprise nucleoside analogs, nucleotide analogs, non-nucleoside analogs, non-nucleotide analogs and others.

Candidate compounds are obtained from a wide variety of sources including libraries of synthetic or natural compounds. For example, numerous means are available for random and directed synthesis of a wide variety of organic compounds and biomolecules, including expression of randomized oligonucleotides, synthetic organic combinatorial libraries, phage display libraries of random peptides, and the like. Candidate compounds can also be obtained using any of the numerous approaches in combinatorial library methods known in the art, including biological libraries; spatially addressable parallel solid phase or solution phase libraries: synthetic library methods requiring deconvolution; the "one-bead one-compound" library method; and synthetic library methods using affinity chromatography selection (Lam, Anti-Cancer Drug Design, 1997, 12:145). Alternatively, libraries of natural compounds in the form of bacterial, fungal, plant and animal extracts are available or readily produced. Additionally, natural and synthetically produced libraries and compounds can be readily modified through conventional chemical, physical, and biochemical means.

Further, known pharmacological agents can be subjected to directed or random chemical modifications such as acylation, alkylation, esterification, amidation, etc. to produce structural analogs of the agents. Candidate compounds can be selected randomly or can be based on existing compounds that bind to and/or modulate the function of MAIL activity. Therefore, a source of candidate agents is one or more library of molecules based on one or more known compounds that increases or decreases MAIL protein expression and/or enzyme activity in which the structure of the compound is changed at one or more positions of the molecule to contain more or fewer chemical moieties or different chemical moieties. The structural changes made to the molecules in creating the libraries of analog activators/inhibitors can be directed, random, or a combination of both directed and random substitutions and/or additions. One of ordinary skill in the art in the preparation of combinatorial libraries can readily prepare such libraries based on the existing compounds.

Assays for the identification of MAIL modulators can be carried out manually or using an automated system. Automated systems are preferred if high throughput screenings are performed. For example, one type of automated system utilizes multi-well culture plates, for example, 96-well, 384-well or 1536-well culture plates, wherein each well can contain cancer cells which express MAIL endogenously, recombinant cells having a nucleic acid encoding the MAIL protein, or the purified MAIL protein.

A High Throughput Screening method to identify MAIL modulators such as antagonists, agonists or inverse agonists is provided. Reagents have been generated which can be used to perform high throughput screening to identify MAIL modulators such as antagonists, agonists or inverse agonists. The role of MAIL in regulation of pro-inflammatory cytokines has been demonstrated in primary human monocytes. However, being primary cells with a relatively short life in culture and due to high donor related variability seen in monocytes, these cells may not be desirable for use in HTS. The development of a novel MAIL over-expressing cell line provides a desirable, stable assay system for HTS.

The purified MAIL protein, any of the antibodies against MAIL polypeptides disclosed herein and the various constructs used to reduce MAIL expression (e.g. perform gene knock-in and gene knock-down studies) can be used in studies for understanding the mechanism of action of an identified MAIL modulator such as an agonist, antagonist, inverse agonist as well as understanding the function of the protein. In other embodiments, the purified MAIL protein, any of the antibodies against MAIL polypeptides disclosed herein and the various constructs used to perform gene knock-in and gene knock-down studies can be used in screening methods such as high throughput screening to identify compounds which are MAIL, modulators such as agonists, antagonists, inverse agonists.

After a compound has been identified that meets the desired criteria for modulating MAIL activity or expression, the compound can then be administered to a live subject, such as a living cell, tissue culture, or other subject expressing MAIL to assess the efficacy. This can be useful to establish toxicity and other pharmacological parameters of the compound important for determining dosing regimens. For example, after a compound is identified using an ex vivo system containing a MAIL polypeptide, the compound can be administered to a culture of cells or an organism afflicted with cancer to examine various pharmacological aspects of the compound. Additionally animal models can be used in conjunction with the nucleotides, antibodies and kits described herein to assess the carcinogenic potential of a compound. The MAIL systems as described herein are particularly advantageous for identifying and establishing dosing regimens in humans, because animals, particularly large species such as canines and primates can be used, which are closer in weight to humans as compared to rats or mice and therefore provide a more suitable animal model for estimating human dosing.

In another embodiment, the invention provides a method of identifying a compound useful for treating cancer, comprising the steps of: (a) contacting a sample expressing MAIL with a test compound; and (b) determining whether the test compound increases or decreases the expression of MAIL. In some embodiments, the method further comprises the steps of: (a) administering the test compound to an animal afflicted with cancer; and (b) determining the extent to which the test compound affects growth of the cancer.

In some embodiments, the animal model of cancer involves a rodent, for example, a rat or mouse; in another aspect the animal model of infection involves a dog, or a primate, for example, monkey or a human.

Therapeutic efficacy and toxicity can be determined by standard pharmaceutical procedures in cell cultures or experimental animals by calculating, for example, the $ED_{50}$ (the dose therapeutically effective in 50% of the population) and the $LD_{50}$ (the dose lethal to 50% of the population). The dose ratio between toxic and therapeutic effects is the therapeutic index, and can be expressed as the ratio, $LD_{50}/ED_{50}$. The data obtained from cell culture assays using MAIL polypeptide, cells expressing MAIL and/or animal studies, such as canine or primate studies, is used in formulating a range of dosage for human use. The dosage contained in such compositions preferably gives rise to a range of circulating concentrations that include the $ED_{50}$ with little or no toxicity. The dosage varies within this range depending upon the dosage form employed, sensitivity of the patient and the route of administration.

The exact dosage will be determined by the one administering the dose, in light of factors related to the subject requiring treatment. Dosage and administration are adjusted to provide sufficient levels of the active agent or to maintain the desired effect, for example, control of bacterial during stationary phase. Factors that can be taken into account include the severity of the infection and other factors, including the general health of the subject, age, weight and gender of the subject, diet, time and frequency of administration, drug combination(s), reaction sensitivities and tolerance/response to therapy.

The pharmaceutical compositions containing a compound that has been identified as modulating MAIL expression or activity can be administered by any number of routes including, but not limited to, oral, intravenous, intramuscular, intruarticular, intraarterial, intramedullary, intrathecal, epidural, intraventricular, transdermal, subcutaneous, intraperitoneal, intranasal, enteral, topical, sublingual, inhalational, intraocular, intra-aural or rectal means.

In addition to the active ingredients, these pharmaceutical compositions can contain suitable, pharmaceutically acceptable carriers comprising excipients and auxiliaries which facilitate processing of the active compounds into preparations that can be used pharmaceutically or which facilitate absorption or distribution of the active compounds. Further details on techniques for formulation and administration can be found in Remington's Pharmaceutical Sciences, Maack Publishing Co., Easton, Pa.

Pharmaceutical compositions for oral administration can be formulated using pharmaceutically acceptable carriers well-known in the art in dosages suitable for oral administration. Such carriers enable the pharmaceutical compositions to be formulated as tablets, pills, dragees, capsules, liquids, gels, syrups, slurries, suspensions and the like, for ingestion by the patient.

EXAMPLES

Example 1

MAIL is Differentially Expressed in LPS Treated Primary Human Monocytes.

To characterize differential gene expression, primary human monocytes were treated with the pro-inflammatory agonist LPS, for 4 hours, followed by RNA extraction and microarray analysis using an in-house developed target microarray chip described infra.

Amongst the target genes, MAIL (Molecule possessing Ankyrin repeats Induced by LPS) (human MAIL amino acid sequence SEQ ID NO: 1 and human MAIL cds SEQ ID NO: 2) was upregulated 4 fold (log fold change is approximately 2) in LPS induced monocytes. As expected, the pleiotropic cytokine IL-6 was upregulated with LPS treatment (Delpedro et al. 1998) (FIG. 1).

Preparation of human monocytes: Briefly, blood was obtained from normal, healthy donors and PBMC were isolated by Ficoll-paque purification (Amersham-Biosciences, Piscataway, N.J.). Cells were plated in RPMI 1640 supplemented with 10% fetal bovine serum and L-glutamine and incubated at 37° C., 5% $CO_2$. Non-adherent cells were removed from the adherent monocytes by washing the plate. Monocytes were treated with LPS (*E. coli* serotype O55:B5) (Sigma-Aldrich, Saint Louis, Mo.), IL-1β, MCP-1, TNF-α (R&D systems Inc. Minneapolis, Minn.), PMA and ionomycin (Sigma-Aldrich) for 4 hours. RNA was extracted using the RNeasy Mini kit (Qiagen Inc., Santa Clarita, Calif.).

The cDNAs printed on the microarrays were from the IMAGE consortium (Integrated Molecular Analysis of Genome and their Expression) and Incyte libraries. All clones were sequence-verified before PCR amplification. The IMAGE clones were purchased from the Human UniGene Library (Research Genetics, Huntsville, Ala.). The cDNAs were PCR amplified directly from 50% glycerol bacterial stock and purified with a Qiagen 96 PCR purification kit, and run on 1% agarose gel to confirm single product amplification. PCR products were then were mixed 1:1 with a 10 Molar NaSCN printing buffer, and printed in duplicate on amino silane-coated slides [GAPs II (Corning, Corning, N.Y.)] by using a Generation III Microarray Spotter (Amersham Biosciences). The spots were about 250 µm in diameter with a 280-µm center-to-center spacing. Printed slides were cross-linked with 500 mJ UV energy, stored under vacuum desiccation overnight, then incubated in isopropanol at room temperature for 10 min, then in distilled water for 2 minutes and centrifuged to dry. Microarrays were then returned to vacuum desiccation until hybridization.

The cDNA spotted array, comprised 8000 clones from various sources: including Incyte, ATCC, Research Genetics (IMAGE consortium) and some clones generating internally from cDNA libraries. The microarray included 30 plant genes for the determination of nonspecific hybridization (gift from Mark Schena, Stanford University). The microarray also included 72 replicates of actin as well as 24 replicates of 8 different spike control genes (Stratagene Spot Report). Two of the spike controls were also added to the chip as a dilution series of 12 spots, at 1:3 dilution intervals, 24 replicates each dilution. There were also 24 arabadopsis thalina genes spotted 8 times each, used as negative controls.

One round of T7 polymerase-based linear RNA amplification was performed by reverse transcription of RNA with a T7 promoter oligo(dT) primer and Cy3-dCTP-labeled fluorescent cDNA probes synthesized from the amplified RNA, except that to degrade the amplified RNA template, RNaseA (10 units) was added and incubated at 37° C. for 20 min, Qiagen columns (Qiagen, Valencia, Calif.) were used instead of Microcon columns, and 5 control spike transcripts from Spot Report kit were added at probe synthesis. Following purification probes were vacuum-dried and resuspended in 50 µl of hybridization buffer [Version 2 hybridization buffer (Amersham Biosciences, Piscataway, N.J.) with 50% formamide] containing human Cot1 DNA (Invitrogen, Carlsbad, Calif.) and 3 pre-labeled cDNA spike controls synthesized from Spot Report transcripts (Stratagene, San Diego, Calif.).

Each probe was hybridized to two microarrays. Prior to hybridization, probes were heated to 95° C. for 2 minutes, left at room temperature for 5 min, then applied to the slides. The slides were covered with glass cover slips, sealed with DPX (Fluka), and hybridized at 42° C. overnight. Slides were washed and scanned with an Agilent G2565AA Microarray Scanner (Agilent Technologies, Palo Alto, Calif.). Fluorescence intensity for each feature of the array was obtained by using Imagene4.2 software (Biodiscovery, Los Angeles, Calif.).

The microarray method was adapted from Salunga, R. C., Guo, H., Luo, L., Bittner, A., Joy, K. C., Chambers, J., Wan, J., Jackson, M. R. and Erlander, M. G., Gene expression analysis via cDNA microarrays of laser capture microdissected cells from fixed tissue. In M. Schena (Ed.), DNA Microarrays a Practical Approach, Oxford University Press, Oxford, 1999.

To examine differential gene expression, hierarchical cluster analysis of the ratios (agonist-treated versus mock-treated control) for all genes changing more than 4-fold in at least 1 of the 5 comparisons was used. Hierarchical cluster analysis was performed with the OmmiViz Pro software package (OmniViz, Maynard, Mass.) using the CorScape visualization. FIG. 1 shows a subset of this analysis identifying MAIL gene expression as being strongly upregulated in human monocytes in response to LPS. The genes are represented by rows with the number demonstrating the relative linear repression or induction ratio as indicated by the number scale at the bottom of the FIG. 1. Fold change (log) for each gene in response to treatment is also presented in each square and may vary from the actual value by +/−1.

Example 2

MAIL Antibody Characterization and Validation of MAILp-silencer for Mail Knock-Down:

For functional characterization of MAIL, anti-MAIL antisera as well as MAIL specific siRNA were developed. Three peptides were synthesized ("M1," SEQ ID NO:6, "M2," SEQ ID NO:7, "M3" SEQ ID NO:8), coupled to KLH and used to immunize rabbits respectively. The polyclonal serum was collected, pooled and tested for specificity against purified MAIL protein by western blotting. Additionally, anti-MAIL antiserum, M456 was obtained by immunizing one rabbit with a pool of three KLH coupled antigenic peptides ("M5," SEQ ID NO:9, "M6," SEQ ID NO:10, "M7" SEQ ID NO:11).

Immunoreactivity of the antiserum to MAIL was determined by western blotting. Purified MAIL was resolved by SDS-PAGE and probed with either the pooled pre-immmune serum or an anti-MAIL antiserum pool consisting of M1, M2, and M3 anti-MAIL antibodies or the anti-MAIL antiserum consisting of M456 anti-MAIL antibodies or after pre-absorption with the MAIL antigenic peptides to show specificity. The western blot was also probed with a his-tag specific antibody to confirm the presence of purified recombinant MAIL. The anti-MAIL antiserum M456 was used to probe either recombinant MAIL purified from *E. coli* or whole cell lysates from his-MAIL over-expressing cells. The anti-MAIL antisera M1, M2, M3 and M456 detect a specific 72 kD band on the western blot. Specificity of the M1, M2, M3 and M456 anti-MAIL antisera was shown by pre-absorbing the antisera with the respective antigenic peptides resulting in loss of detectable MAIL signal on the western blot.

The M1, M2, M3 antibody pool was used to show that the siRNA sequence can effectively knock-down MAIL protein expression. HEK293 cells were co-transfected with a vector expressing GST tagged MAIL (GST-MAILpDest27) and either the psilencer 1.0 vector (psil) or MAIL-psilencer construct (MAIL-psil, as described below). 48 hours later, cells were lysed with RIPA buffer and GST-tagged MAIL was pulled down with glutathione beads, immunoblotted and MAIL expression was quantified using the anti-MAIL and also the anti-GST-tag antibodies. This short hairpin RNA (shRNA) construct was used for elucidating the role of MAIL in primary human monocytes.

MAIL antibody generation: Antigenic peptide design: Rabbit polyclonal antibodies to human MAIL were generated using antigenic and surface exposed peptide sequences predicted by the algorithm of Hopp/Woods. An amino- or carboxy-terminal cysteine residue was added to the peptide, if required, to allow coupling to activated KLH.

Generation of anti-MAIL antibodies: 2 mg of synthetic peptide was reconstituted into conjugation buffer and coupled to activated KLH (Pierce Biotechnology, Rockford, IL) by stirring for 2 hours, diluted with PBS, and aliquoted for the immunization of rabbits. Anti-MAIL (human) antibodies were generated by immunizing rabbits with either M1 (SEQ ID NO: 6) or M2 (SEQ ID NO: 7) or M3 (SEQ ID NO: 8) peptide, each coupled to KLH, or with a pool of KLH coupled peptides M4 (SEQ ID NO: 9), M5 (SEQ ID NO: 10) and M6 (SEQ ID NO: 11). M1, M2 and M3 polyclonal serum was pooled in equal volumes to generate the M1, M2, M3 antiserum pool.

Cloning and expression of recombinant MAIL protein: MAIL was amplified by RT-PCR from LPS treated human monocytes' RNA and cloned into the pENTR-dTOPO vector (Invitrogen Corp, Carlsbad, Calif.) using primers (SEQ ID NO:12) 5'-CACCATTGTGGACAAGCTGCTGGAC-3' and (SEQ ID NO:13) 5'-CTAATACGGTGGAGCTCTCT-GCTGA-3'. PCR conditions were as follows: 1 cycle, 95° C., 2 min; 35 cycles (95° C., 1 min; 58° C., 1 min; 72° C., 5 min), followed by 1 cycle, 72° C., 10 min using pfu turbo polymerase (Stratagene, La Jolla, Calif.), with 5% DMSO in the reaction. The MAIL 2155 bp PCR product was ligated into the pENTR-dTOPO vector (Invitrogen) as per manufacturer's instructions and transfected into the company's provided competent cells as per manufacturer's instructions. The pENTR-MAIL clones were identified by SacI digestion generating 1.4 kb and 3.8 kb fragments. The pENTR-MAIL vector was created so that the start codon from the MAIL coding sequence is deleted. This vector was used for generation of pDEST26-hisMAIL and GST-MAIL expression vectors.

In addition, a full-length MAIL-pENTR clone (pENTR-FL-MAIL) was generated using the same PCR conditions described above for pENTR-MAIL except that the 5' primer used was 5'-CACCATGATTGTGGACAAGCTGCTGGA-3' (SEQ ID NO:14). Subsequent AvaI digestion produced ~280 bp, ~450 bp, and 4.2 kb fragments to confirm directional ligation. pENTR-FL-MAIL clone was confirmed by sequencing (Sequetech, Calif.). The pENTR-FL-MAIL vector was used for generation of the untagged MAIL expression vectors, including the plenti-MAIL and MAILAdC20.

For *E. coli* expression of his-tagged MAIL (his-MAIL) protein, the pENTR-MAIL plasmid was recombined with the pDEST17 vector (Invitrogen) as per manufacturer's instructions and utilizing manufacturer's competent cells. Positive clones were identified by HindIII digestion, producing 1.7 kb and 5.8 kb fragments. Clones were confirmed by SacI digestion, releasing 1.4 kb and 6 kb fragments. Mammalian expression of his-MAIL was accomplished by recombination of pENTR-MAIL with pDEST26 (Invitrogen) to create a pDEST26-hisMAIL plasmid. Similarly, recombinant GST-tagged MAIL (GST-MAIL) was generated by recombination of pENTR-MAIL with pDEST27 (Invitrogen) to create a pDEST27-GST-MAIL plasmid. These plasmids were transfected into mammalian cells for constitutive protein expression using Lipofectamine 2000 (Invitrogen) as described herein. His-MAIL protein was also over-expressed in SF9 cells (using Gateway vector pDEST10). Untagged MAIL was cloned into the pENTR-dTOPO vector using PCR conditions described earlier. Primers used were, 5'-CACCATGAT-TGTGGACAAGCTGCTGGA-3' (SEQ ID NO:14) and 5'-CTAATACGGTGGAGCTCTCTGCTGA-3'(SEQ ID NO:15). This full-length construct was used for the generation of lentiviral constructs.

Purification of his-MAIL: pDEST17-hisMAIL plasmid was transformed into BL21-A1 *E. coli* (Invitrogen) cells and protein expression was induced by L-arabinose for 4 hours at 30° C. Bacterial pellets were sonicated and incubated at 4° C. for 1 hour in denaturing lysis buffer (8M urea, 500 mM NaCl, EDTA free protease inhibitor cocktail (Roche Molecular Biochemicals, Indianapolis, Ind.)). Recombinant his-MAIL protein was purified from sonicated lysates by Hi-Trap $Ni^+$ column chromatography (Amersham Biosciences) as per manufacturer's instructions, but with all solutions containing 8M urea. Purified his-MAIL protein was resolved on 7% Tris-Acetate SDS-PAGE gels (Invitrogen), transferred to nitrocellulose membranes, and analyzed by western blot analysis.

Transient transfection of HEK293 and preparation of cell lysates: $2\times10^6$ cells were plated in a 6 well plate overnight. A lipid and DNA complex consisting of 10 μl Lipofectamine 2000 (Invitrogen) and 4 μg plasmid (pDEST27-MAIL) were added to each well. Cells were harvested 24 hours post-transfection using RIPA lysis buffer (50 mM Tris HCl pH8, 150 mM NaCl, 1% NP-40, 0.5% Sodium deoxycholate, 0.1% SDS, EDTA-free protease inhibitors cocktail (Roche Molecular Biochemicals)).

Western blotting: 100 ng purified his-MAIL protein was loaded in each lane of a 7% Tris-Acetate SDS-PAGE gel. The electrophoresed proteins were transferred onto nitrocellulose membrane and the strips were probed individually with either 1:2000 dilution of pooled pre-immune sera, anti-MAIL antibodies, or the competition mix to test for specificity of the MAIL antibody. The competition was set up by pre-incubating the pooled anti-MAIL antibodies with the pooled antigenic peptides at a ratio of 2 μg/ml antibodies to 20 μg/ml antigen. A horse-radish peroxidase conjugated anti-rabbit secondary antibody (Santa Cruz Biotechnology Inc, Santa Cruz, Calif.) was used at a dilution of 1:10,000, blots were developed with ECL plus reagent (Amersham Biosciences) and exposed to X-ray films for imaging.

MAIL Silencer construct: MAIL sequence, 5'-GGUG-UUCGGGUAAAGAACU-3' (SEQ ID NO: 5) (position 385404, of accession number NM_031419, SEQ ID NO:2) was used to design the MAIL specific shRNA and cloned into the psilencer 1.0 vector using the manufacturer's guidelines (Ambion Inc, Austin, Tex.). SEQ ID NO:5 is the antisense of the MAIL mRNA sequence. The MAIL specific shRNA (SEQ ID NO: 5) targets the complementary MAIL mRNA sequence, 5'-AGTTCTTTACCCGAACACC-3', which is provided as SEQ ID NO:22. Clones were screened by restriction enzyme digestion and confirmed by sequencing (Sequetech Corp. Mountain View, Calif.).

GST-MAIL pulldown: To test whether MAILpsil could knock-down MAIL protein expression, HEK293 cells were transiently co-transfected with pDEST27-MAIL and MAILpsil or pDEST27-MAIL and psil vector alone. Cell lysates were prepared using RIPA lysis buffer. GST tagged MAIL in each lysate was pulled down with Glutathione beads (Amersham Biosciences). The beads were separated, washed and boiled in Laemli buffer to elute protein. The eluates were resolved on 10% SDS PAGE gels, transferred onto nitrocellulose membrane and MAIL expression was quantified using the anti-MAIL antibodies. Anti-GST tag and anti-his tag antibodies (Amersham Biosciences) were used to visualize the GST or his tagged MAIL protein respectively. Anti-GAPDH antibodies (Chemicon International, Temecula, Calif.) were used for demonstrating equal loading in each lane. To show specificity of the M1, M2, and M3 anti-MAIL antibodies, competition was set up by pre-incubating the pooled anti-MAIL antibodies with the pooled antigenic peptides at a ratio of 2 µg/ml antibodies to 20 µg/ml antigen. A horse-radish peroxidase conjugated anti-rabbit secondary antibody (Santa Cruz Biotechnology Inc) was used at a dilution of 1:10,000, blots were developed with ECL plus reagent (Amersham Biosciences) and exposed to X-ray films for imaging.

Example 3

MAIL is Essential for IL-6 Induction.

Based on reports suggesting a role for MAIL in LPS induced IL-6 expression, gene knock-down experiments were performed using the MAILpsil construct. Primary human monocytes were transfected with either the vector alone or MAILpsil and 48 hr later treated with LPS for 4 hr. To assess the role of MAIL in regulation of IL-6 expression, secreted IL-6 in culture supernatants was measured using ELISA. In the presence of MAILpsil and absence of LPS stimulation, IL-6 secretion was reduced by ~90% (FIG. 2) in comparison to psil alone. Knocking down or reducing MAIL expression also resulted in decreasing LPS induced IL-6 secretion by ~61%. These findings confirmed the importance of MAIL, in regulation of IL-6 expression.

Silencing MAIL Reduces IL-8 and MCP-1 Secretion

To determine whether MAIL is also involved in regulation of other inflammatory cytokines, the culture supernatants were tested using a 23 human cytokine array (Raybiotech Inc, Norcross, Ga.). Knocking down or reducing MAIL expression with MAILpsil resulted not only in a decrease in IL-6 expression but also in significant decreases in IL-8 and MCP-1 secretion from unstimulated as well as LPS stimulated monocytes. To quantitate this difference, IL-8 and MCP-1 ELISAs were performed on the culture supernatants (FIG. 3a, 3b). Standard paired t test was performed to determine statistical significance. Silencing the MAIL gene resulted in a 70% decrease in IL-8 secretion in uninduced monocytes (n=4, $\alpha$=0.05, p=0.008) and a 56% decrease in IL-8 secretion in LPS induced monocytes (n=4, $\alpha$=0.05, p=0.003). In response to MAILpsil, secreted MCP-1 was decreased by 60% in uninduced cells (n=4, $\alpha$=0.05, p=0.025) and by 75% in LPS induced monocytes (n=4, $\alpha$=0.05, p=0.09). Although the LPS induced increase in IL-8 and MCP-1 secretion was modest, the effect of MAIL silencing was apparent. MAILpsil also downregulated the basal expression of IL-12p40 (FIG. 3c).

Monocyte transfections: Primary human monocytes were isolated as described earlier. $5 \times 10^6$ monocytes were transfected by mixing 2 µg plasmid with 3 µl Dosper (Roche Molecular Biochemicals) and incubating the DNA and lipid mix on ice for 30 min. MAIL knock down assays were performed at 48 hr post transfection. Cytokine Arrays and ELISA: IL-6, 1-8 and MCP-1 ELISA kits (Amersham Biosciences) were used to quantitate the respective cytokines in each sample. Each step was performed as directed by the manufacturer, and the plates were read at 450 nm using a SpectraMaxPlus-384 spectrophotometer (Molecular Devices Corp, Sunnyvale, Calif.). The human cytokine array was purchased from Raybiotech Inc and used as per the manufacturer's instructions. The chemiluminescent signal was captured using the Lumiimager (Roche Molecular Biochemicals, Indianapolis, Ind.).

Example 4

MAIL is Downregulated by Dexamethasone:

Anti-inflammatory glucocorticoids such as dexamethasone (dex) are known to downregulate expression of cytokines such as IL-6 and TNF-$\alpha$. The exact mechanism of action for glucocorticoids is unclear. Reports suggest that dex may negatively regulate IL-6 expression by reducing IL-6 mRNA stability and NF-$\kappa$b translocation to the nucleus. However, it is entirely possible that more than one mode of action for dex is responsible for reducing IL-6 expression. Since dex also downregulates LPS induced IL-6, experiments were performed to determine whether MAIL expression is affected by dexamethasone. Monocytes were treated with LPS in the presence or absence of dexamethasone 21 acetate (Sigma-Aldrich) for and, IL-6 secretion was measured using ELISA and RT-PCR. As expected a significant decrease in IL-6 expression upon dex treatment was observed. MAIL mRNA levels were quantified by RT-PCR (FIG. 4a). In comparison to untreated cells, a 7 fold increase MAIL mRNA was observed with LPS treatment (paired t-test, $\alpha$=0.05, p<0.0001). Dex treatment resulted in a 3 fold decrease in MAIL expression (paired t-test, $\alpha$=0.05, p=0.0095) and addition of dex also resulted in lowering LPS induced MAIL expression by 2 fold (paired t-test, $\alpha$=0.05, p=0.014). Thus MAIL expression under the above experimental conditions was directly correlated with IL-6 expression.

Monocyte treatments: Primary human monocytes were isolated as described earlier in Example 1. Cells were treated with 1 µg/ml LPS in the presence or absence of 100 nM dex for 4 hours. Cell supematants were harvested for ELISA and RNA was isolated from the cells using RNeasy® Mini kit (Qiagen Inc., Santa Clarita, Calif.). Quantitative RT-PCR: One-step RT-PCR was performed using the LightCycler (Roche Molecular Biochemicals) with the RNA Amplification Kit, SYBR Green I (Roche Molecular Biochemicals). Briefly, total RNA was isolated using the RNeasy® Mini Kit (Qiagen Inc.), and 100-200 ng of total RNA was used for each RT-PCR reaction with 40 nM MgCl2 and 60 µM of each primer. The reverse transcription step performed at 55° C. for 20 minutes was followed by the PCR conditions: 95° C., 30 seconds and 45 cycles of 95° C., 2 seconds; 58° C., 10 seconds; 72° C., 10 seconds; 1 µl DMSO was added to the reaction with single acquisition at 84° C. Primers used for MAIL were 5'-CCGACTTCTCCTCTGCCTCG-3' (SEQ ID NO: 3) and 5'-GGTGGTGTCAAAATTGGGA-3' (SEQ ID NO:4). TLR4 PCR was performed with primers 5'-CAGAG-GCAGCTCTTGG-3' (SEQ ID NO:16) and 5'-CAGTCCT-CATCCTGGC-3' (SEQ ID NO:17) whereas the CD14 PCR was performed using primers 5'-AGC-CGTTTCTAAAGCGC-3' (SEQ ID NO:18) and 5'-CACGA-CACGTTGCGTAGG-3' (SEQ ID NO: 19). Both TLR4 and CD14 RT-PCR reaction conditions were similar to the MAIL RT-PCR except that the data acquisition temperature was 90° C. and no DMSO was added. Primers used for b-actin amplification were 5'-TCCTGTGGCATCCACGAAAC-3' (SEQ ID NO:20) and 5'-GAAGCATTTGCGGTGGACGAT-3' (SE ID NO:21). b-actin was used for assessing RNA quality and for normalization in all quantitative analyses. All PCR products were verified by sequencing (Sequetech).

Example 5

Downregulation of MAIL by Dex is Independent of TLR4 Expression.

Figure 4:
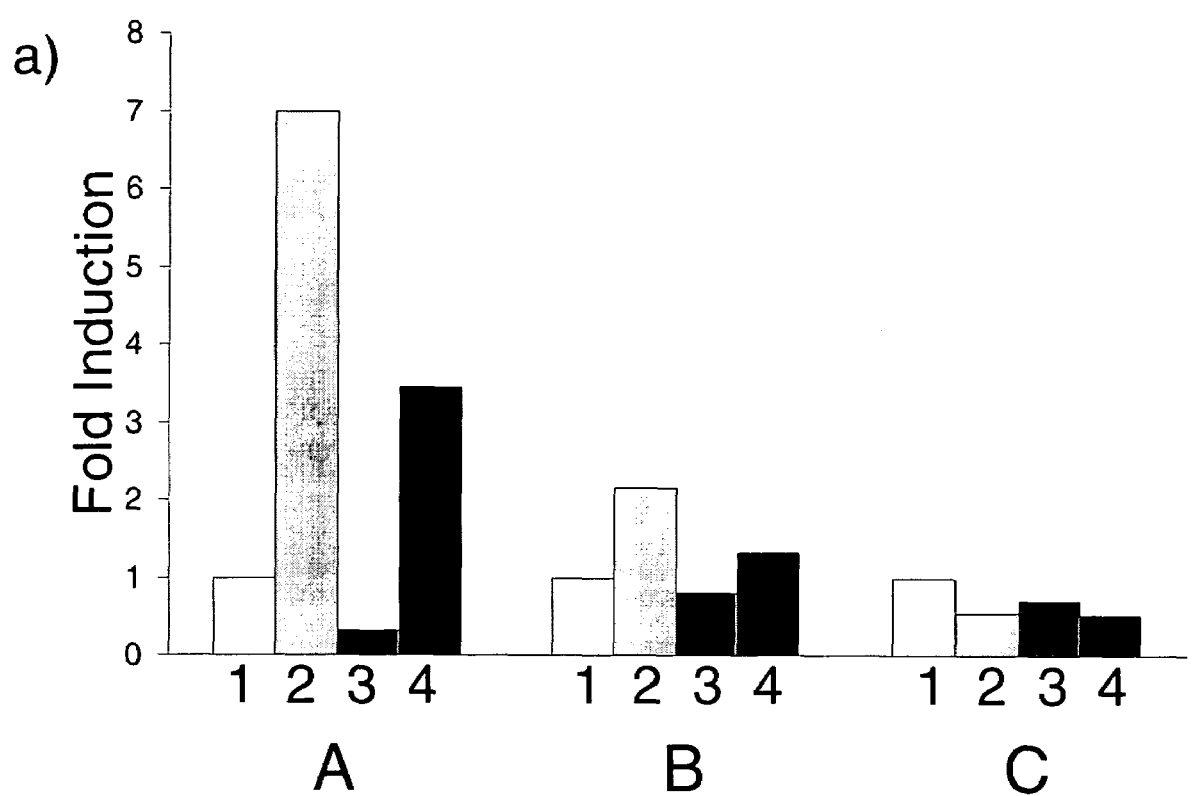
FIG. 4a, dex downregulates basal as well as LPS induced MAIL expression but does not alter TLR4 expression. MAIL (Set A), TLR4 (Set B), and CD14 (Set C) expression was evaluated by quantitative RT-PCR in either untreated primary human monocytes (Sample 1), cells treated with LPS (Sample 2) or dex (Sample 3) or cells co-stimulated with LPS and dex (Sample 4) for 4 hours respectively.
FIG. 4b, CD14 and TLR4 surface expression is not altered by dex treatment. Cell surface expression of CD14 (Column 1) and TLR4 (Column 2) in primary human monocytes upon treatment with LPS (Row A) or dex (Row B), or co-stimulation with dex and LPS (Row C) was analyzed using FACS. Isotype controls are shown as dotted lines, untreated monocytes are represented as solid lines and LPS, dex, or LPS/dex treated samples are shown as heavy solid lines in each panel.
Figure 4:
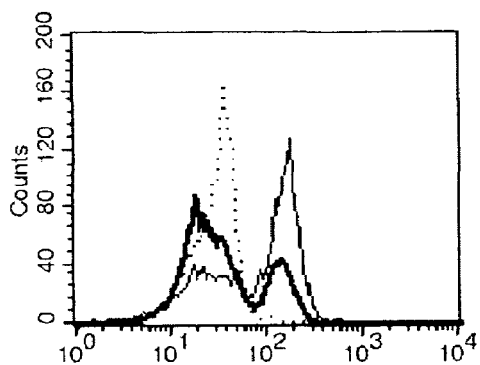
Figure 4:
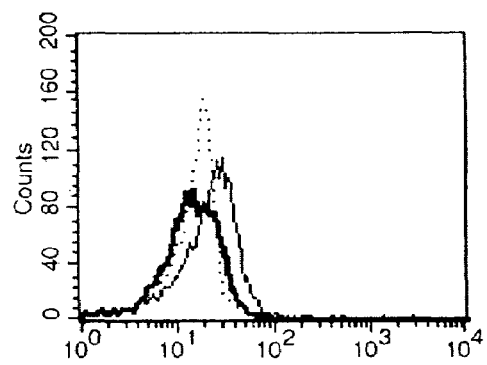
Figure 4:
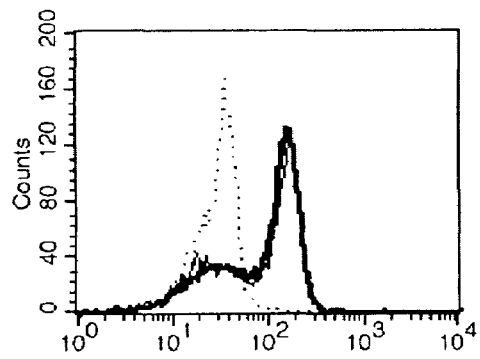
Figure 4:
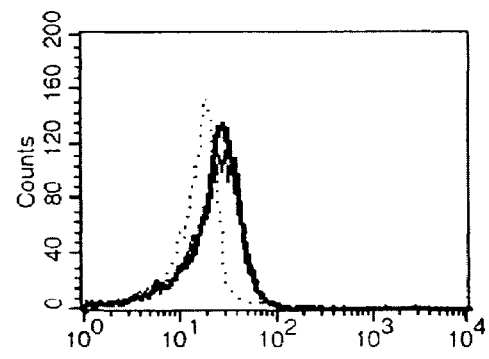
Figure 4:
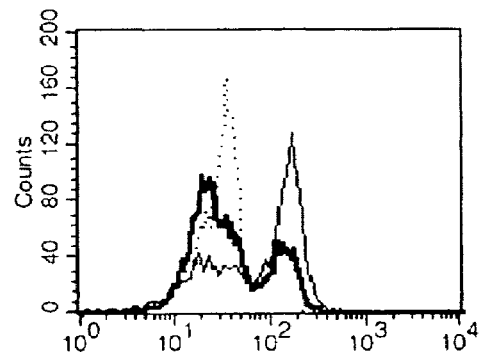
Figure 4:
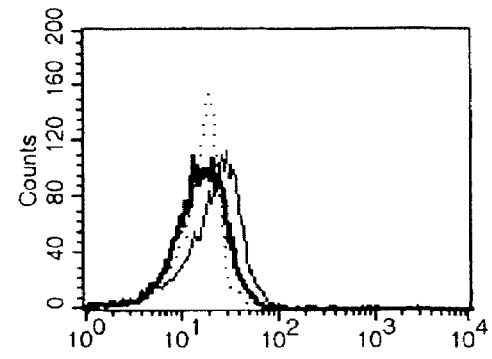

It has been shown previously that signaling through the TLR4 receptor is essential for MAIL expression (Kitamura et al. 2002). Since LPS induced activation of monocytes involves the CD14 and TLR4, CD14 and TLR4 expression in response to dex treatment was assessed. Both mRNA levels as well as surface expression of CD14 and TLR4 were analyzed (FIG. 4). RT-PCR quantification (FIG. 4*a*) revealed that there is a 2-fold increase in TLR4 mRNA expression upon treatment with LPS (paired t-test, $\alpha=0.05$, $p=0.0056$). However, there is no significant change in TLR4 mRNA on dex treatment in the presence (paired t-test, $\alpha=0.05$, $p=0.09$) or absence of LPS stimulation (paired t-test, $\alpha=0.05$, $p=0.031$). The apparent changes in CD14 mRNA levels in the different treatments were not statistically significant (stimulation with LPS alone, paired t-test, $\alpha=0.05$, $p=0.16$; with dex alone, paired t-test, $\alpha=0.05$, $p=0.35$, with dex and LPS, paired t-test, $\alpha 0.05$, $p=0.96$). FACS analysis was performed to analyze surface expression of TLR4 and CD14 in the dex or LPS treated monocytes (FIG. 4*b*). These experiments revealed that 65% of the untreated population expressed CD14. The surface expression of CD14 was decreased to 25% with LPS treatment but was completely unaffected by dex treatment. 35% of the untreated monocytes expressed the TLR4 on the surface. Similar to CD14, TLR4 surface expression was greatly reduced with LPS treatment (to 7.5%) but remained unaffected upon dex treatment. Thus the dex induced downregulation of MAIL expression is not due to the absence of TLR4 signaling.

Flow cytometry: Anti-TLR4-biotin, PE-streptavidin and FITC conjugated anti-CD14 antibodies, along with the isotype control antibodies were purchased from BD-Biosciences Clontech, Palo Alto, Calif. Cells were incubated with human serum (Sigma-Aldrich) to block non-specific binding, double stained as per manufacturer's protocol and fixed in 2% paraformaldehyde prior to analysis. Flow cytometric analysis was performed on a FACSCALIBUR flow cytometer and Cell-quest software (Becton Dickinson & Company, Franklin Lakes, N.J.) was used for data analysis.

Example 6

Over-Expression of MAIL in HEK293 Results in Over-Expression of IL-6.

The MAIL gene from pENTR-FL-MAIL was inserted into the AdC20 vector by Galapagos, Belgium. MAIL was over-expressed in HEK293 cells using the resulting vector MAIL-AdC20. An empty capsid adenovirus AdC20 was used as a control. IL-6 levels were found induced in an MOI dependent manner (FIG. 5). No additional increase in IL-6 induction with LPS stimulation was observed. This cell line can also be used for screening of MAIL agonists/antagonists.

Transductions: MAIL from the pENTR-FL-MAIL vector was inserted into the AdC20 vector by Galapagos, Belgium. The resulting MAILAdC20 packaged vector was added to HEK293 cells. 24 hours later, culture supernatants were analyzed for IL-6 by ELISA.

Over-Expression of MAIL in Human Monocytes Results in Over-Expression of IL-6.

The pENTR-FL-MAIL clone was sent to Tranzyme, where the MAIL sequence was subcloned into the pLenti-puro expression vector. (Tranzyme, Research Triangle Park, N.C.). MAIL was over-expressed in primary human monocytes using either a lentiviral vector alone or a lentiviral vector plenti-MAIL-puro. 48 hours later, cell supernatants were harvested and analyzed either with ELISA or cytokine arrays. Cells were harvested and RNA was isolated using the RNeasy Mini Kit (Qiagen) and employing the manufacturer's instructions. High levels of IL-6 were induced upon MAIL overexpression. Additionally, higher levels of MCP-1, MCP-2, IL-8 and Gro were also induced in MAIL over-expressing human monocytes. These cells could potentially be used for elucidating the role of MAIL in inflammation or screening of MAIL modulators such as agonists, antagonists and inverse agonists.

Over-Expression of MAIL in THP-1 Results in Over-Expression of IL-6 and IL-10 with LPS Challenge.

To elucidate the function of MAIL, a THP-1 clone stably expressing MAIL (MAIL-THP-1) was generated. To account for possible artifacts resulting from lentiviral transduction, a THP-1 cell line that was stably transduced with the vector alone (Control) was also generated. Control THP-1 and MAIL-THP-1 cells were stimulated with LPS for different lengths of time and the culture supernatants were analyzed by either ELISA or cytokine arrays. MAIL-THP-1 cells secreted higher levels of IL-6 with LPS treatment in comparison to the control cells. Interestingly induction of IL-10 in LPS stimulated MAIL THP-1 cells suggesting a role for MAIL in regulation of pro- as well as anti-inflammatory responses (as shown in FIG. 6).

Stimulation of the MAIL-THP-1 cells resulted in adherence of the cells to the surface of the well bottom, whereas the Control-THP-1 cells remained non-adherent. To test whether MAIL over-expression results in differentiation of the THP-1 cells into a more mature monocyte-like phenotype the expression of the cell surface markers such as CD11b, CD11c, CD16, CD14, HLA-DR and HLA-A,B,C was analyzed using flow cytometry. These markers are expressed in mature monocytes or macrophages. It was shown that expression of CD16 and HLA-DR is higher on the MAIL-THP1 cells whereas no difference was observed between the CD14, HLA-A,B,C levels, CD11b or CD11c (Table 1).

It has been previously shown that LPS activation of human dendritic cells results in modification of Histone H3 leading to increased expression of various pro-inflammatory genes (Weinmann et al. 2001). To assess the possible role of MAIL in chromatin modification events, MAIL-THP-1 and the control THP-1 cells (uninfected or cells transduced with the empty lentiviral construct) were treated with LPS for the indicated times (as shown in FIG. 7). Supernatants were harvested and profiled for cytokine production by ELISA. The cell-lysates were used for western blotting and sequentially probed to determine the global effect of Histone H3 modifications. The Histone H3 modifications pursued were, phosphorylation at serine 10, acetylation at lysine 14, Lys 9 or Lys 18. GAPDH levels were determined in each sample and used to show equal loading. In comparison to the control-THP-1 cells, global levels of phoshorylation at H3 (ser10) as well as acetylation at H3 (Lys14) in the MAIL-THP-1 cells, were much higher. There was no to weak acetylation of Histone 3 at Lys9/18 and there was no difference between the control THP-1 and MAIL-THP-1 cells. Generation of Control-THP-1 and MAIL-THP-1 cells: THP-1 cells were transduced with either the lentiviral vector (plenti-puro/empty) alone or plenti-MAIL-puro (Tranzyme Pharma). Cells were selected and clones maintained with 1 μg/ml Puromycin (Sigma-Aldrich).

Flow Cytometry: Uninfected THP-1, Control THP-1, and MAIL-THP-1 cells were immunostained with anti-CD 11b (R&D Systems mc, Minneapolis, Minn.), anti-CD11c (R&D Systems), anti-CD16, anti-CD 14, anti-HLA-DR and anti-HLA-A,B,C antibodies (BD Biosciences Clontech) using a FACSCALIBUR Flow Cytometer™. Data was analyzed using Cell Quest™ software (Becton Dickinson).

Histone H3 modification analysis: Cell lysates were prepared from LPS treated cells using RIPA buffer described in Example 1. Lysates were resolved on a 10% SDS-PAGE gels, blotted onto nitrocellulose membranes and probed sequentially with anti-phospho-histone H3 (Ser10), anti-acetyl-histone H3 (Lys 14), anti-acetyl histone H3 (Lys9/18) antibodies (Upstate USA Inc, Charlottesville, Va.) and anti-GAPDH antibodies (Chemicon) for normalizing protein loading. HRP conjugated anti-rabbit or anti-mouse antibodies were used for detection (Santa Cruz Biotechnology). After each probing, the blots were stripped with Restore buffer (Pierce), washed, and blocked again before re-probing. Histone H3 modification signal vs. GAPDH signal ratios were calculated for each time point using the LumiAnalyst software (Roche, version 3.1).

TABLE 1

| | % Positive cells ± SEM | | | |
|---|---|---|---|---|
| | plenti-dsRED-THP1 | MAIL-THP1 | Difference in mean | P value |
| CD11b | 32.22% ± 4.33 | 46.58 ± 4.66 | 14.36 ± 6.09 | n = 4, $\alpha \subset 0.05$, p = 0.099 |
| CD16 | 0.55% ± 0.15 | 1.56% ± 0.31 | 1.01% ± 0.20 | n = 4, $\alpha \subset 0.05$, p = 0.015* |
| HLA-DR | 33.58% ± 3.55 | 52.39% ± 0.15 | 18.8% ± 3.69 | n = 3, $\alpha \subset 0.05$, p = 0.036* |

Example 7

MAIL is Expressed at Higher Levels in Cancer Tissues.

MAIL expression in multiple malignant cancer tissues was examined by IHC and compared to a pre-immune control staining. No staining was observed when the antibodies were pre-incubated with the antigenic peptide pool prior to probing. Tissue sections on microscopic slides were dewaxed and re-hydrated. Slides were microwaved for 5 min in Target buffer (Dako, Carpenturia, Calif.), cooled, placed in phosphate-buffered saline (PBS, pH 7.4) and treated with 3% (v/v) $H_2O_2$ for 10 minutes at room temperature. All incubations (30 minutes each) and washes were performed at room temperature. Normal rabbit blocking serum (Vector Labs, Burlingame, Calif.) was placed on all slides for 10 minutes. After a brief rinse in PBS, sections were treated with rabbit polyclonal MAIL primary antibody (M456). The substitution of the primary antibody with the antibody dilution buffer (Zymed, San Francisco, Calif.) was used as a negative control. To ensure that the staining was specific, the primary antibody was pre-incubated at a ratio of 1:10 with pooled antigenic peptides (M4, M5 and M6) in the antibody dilution buffer, overnight at 4° C. Slides were then washed in PBS and treated with goat anti-rabbit biotinylated secondary antibodies (Vector Labs). After washing in PBS, the avidin-biotin-horseradish peroxidase complex reagent (HRP, Vector Labs) was added. All slides were washed and treated with 3,3'-diaminobenzidine (DAB, Biomeda, Foster City, Calif.) two times for 5 minutes each, rinsed in distilled water, and counterstained with hematoxylin.

No detectable immunolabeling was observed in the negative control. MAIL immunolabeling was presented as brown staining. All tissues were graded by the intensity of the brown staining cells (scores: 0=no detectable staining; 1=weak, light brown staining; 2=moderate, brown staining; 3=strong, dark brown staining). All scores were averaged per group and then plotted. Very weak MAIL immunolabeling was detected in T cell lymphomas, synovial sarcoma, seminoma, rhabdomyosarcoma, Leiomyosarcoma, kidney cancer, fibrosarcoma and Ewings sarcoma (average score=0.5), glioma, ovarian yolk sac tumor (endodermal sinus tumor), melanoma, medulloblastoma, Hodgkin's disease and B cell lymphoma (score=1). Weak to moderate staining was observed in pancreatic cancer, endometrical cancer, prostate cancer, esophagus cancer, thyroid cancer, skin squamous cell cancer, neuroblastoma, nerve sheath malignant tumor, lung cancer, colon cancer, skin basal cell cancer (score range 1.15 to 1.5); urinary bladder, liver cancer, stomach cancer, mesothelioma, gastric, esophagus, cervical and rectal and ovarian cancer (score range 1.7 to 2.05), while more intense MAIL immunolabeling was detected in colon cancer, osteosarcoma, gastro stromal tumor and breast cancer (score range 2.4 to 3). These data suggest an up-regulation of MAIL is associated with various cancer pathologies.

MAIL is Expressed at Higher Levels in Malignant Breast Cancer Tissues.

MAIL expression in normal, benign, and malignant breast cancer tissue was examined by IHC and compared to a pre-immune control staining of malignant tissue. Normal, benign and malignant breast cancer tissue sections were analyzed for MAIL expression and IL-6 expression using immunohistochemistry. Briefly, ReceptorGrid™ checkerboard slides (M90; lot#3284) were purchased from (Biomeda Corp., Foster City, Calif.). Each slide contained a paraffin section of normal (n=13), benign (n=8) and malignant (n=31) human breast tissues. Tissue sections on microscopic slides were dewaxed and re-hydrated. Slides were microwaved for 5 min in Target buffer (Dako, Carpenturia, Calif.), cooled, placed in phosphate-buffered saline (PBS, pH 7.4) and treated with 3% (v/v) $H_2O_2$ for 10 minutes at room temperature. All incubations (30 minutes each) and washes were performed at room temperature. Normal rabbit blocking serum (Vector Labs, Burlingame, Calif.) was placed on all slides for 10 minutes. After a brief rinse in PBS, sections were treated with rabbit polyclonal MAIL primary antibody or goat anti-human IL-6 antibody (R&D systems). The substitution of the primary antibody with the antibody dilution buffer was used as a negative control. Slides were then washed in PBS and treated with goat anti-rabbit biotinylated secondary antibodies (Vector Labs). After washing in PBS, the avidin-biotin-horseradish peroxidase complex reagent (HRP, Vector Labs) was added. All slides were washed and treated with 3,3'-diaminobenzidine (DAB, Biomeda, Foster City, Calif.) two times for 5 minutes each, rinsed in distilled water, and counterstained with hematoxylin.

No detectable immunolabeling was observed in the negative control. MAIL immunolabeling was presented as brown staining. All tissues were graded by the intensity of the brown staining in the breast epithelial/tumor cells (scores: 0=no detectable staining; 1=weak, light brown staining; 2=moderate, brown staining; 3=strong, dark brown staining). All scores were averaged per group and then plotted. Weak MAIL immunolabeling was detected in the normal (average score=0.7) and benign, fibroadenoma cells (score=1.0), while more intense MAIL immunolabeling was detected in the malignant breast cells (score=2.3). These data suggest an up-regulation of MAIL is associated with a malignant phenotype of human breast epithelial cells.

Figure 8:
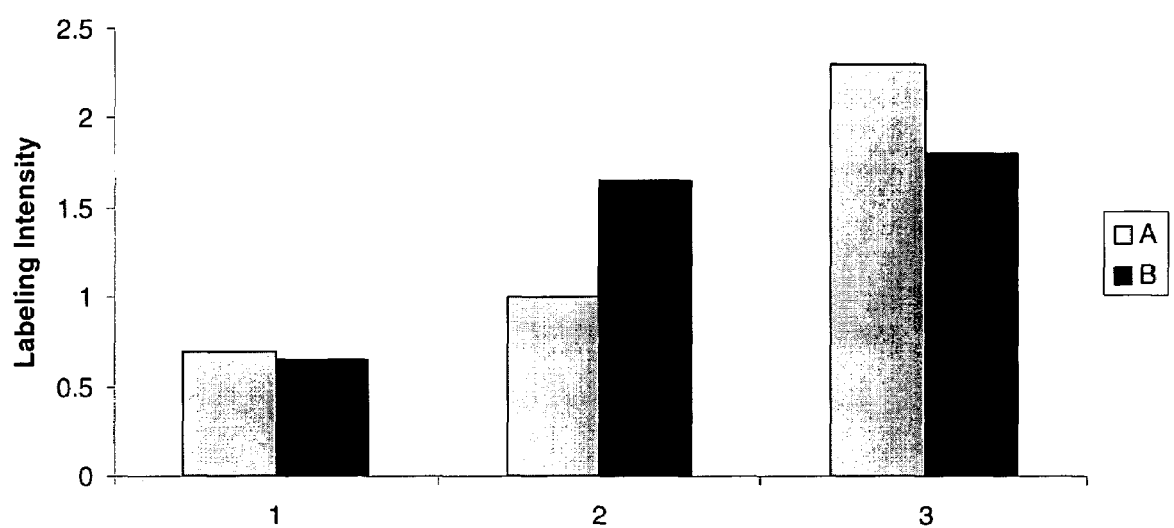
FIG. 8, Immunohistochemical analysis of MAIL expression in breast cancer tissue. MAIL (Set A) and IL-6 (Set B) protein expression was measured by IHC in normal [n=13] (Sample 1), benign [n=8] (Sample 2), and malignant breast cancer tissue [n=31] (Sample 3).

To correlate the expression of MAIL with IL-6 in breast cancer tissues, a grading scheme identical to that used for MAIL expression was used. Weak immunostaining was detected in the normal (average score=0.7) cells, while more intense IL-6 immunolabelling was observed in benign and malignant tissues (average score=1.5) as shown in FIG. 8.

Example 8

Method of Identifying Compounds as Mail Modulators Such as Agonists, Inverse Agonists and Antagonists:

Cells such as HEK293, THP-1 or U937 or primary human monocytes which express MAIL either stably, as for example with the cell line MAIL-THP-1, or transiently upon transduction with MAILAdC20 or pLenti-MAIL are plated in a multi-well tissue culture plate. Upon application of a compound or material, MAIL agonists result in either an increase in MAIL mRNA measured by RT-PCR, MAIL protein or an upregulation of one or more MAIL induced cytokines/chemokines such as IL-6, IL-8, MCP-1, MCP-2, Gro and LPS induced IL-10. Upon application of a compound or material which acts as a MAIL agonist when applied on monocytic cells such as THP-1, an increase in cells adhering to the culture well are observed. MAIL agonists can be determined using a quantitative assay such as ATP-lite (Perkin Elmer, Mass.). Application of a compound or material which acts as a MAIL agonist when applied on monocytic cells such as THP-1 also results in increased surface expression of markers such as HLA-DR, CD16 or CD11b. These cytokines/chemokines can be measured using common ELISA techniques well known in the art. Upon application of a compound or material which acts as a MAIL antagonist, MAIL mRNA and/or MAIL protein expression increases which decreases expression of one or more MAIL induced cytokines/chemokines such as IL-6, IL-8, MCP-1, MCP-2, Gro and LPS induced IL-10.

Example 9

Use of MAIL as a Marker for Cancer:

MAIL mRNA or MAIL proteins are used as markers to compare clinically diagnosed tumor tissues and adjacent tissue at the mRNA level by RT-PCR or at the protein level using the antibodies described herein to identify potentially cancerous tissues. RT-PCR or IHC, ELISA, western blotting or immunoprecipitation is employed to identify tissue which is cancerous. Samples or biopsies of the tissues are collected from a patient. The diagnosed tumor tissue contains a level of the marker, MAIL which is compared to the adjacent tissues. The samples are processed according to the technique being employed and the levels of MAIL mRNA or MAIL protein are compared in the tissues.

If similar or increased levels of MAIL mRNA or MAIL protein are detected in the adjacent tissue, the tissue can be subjected to further tests to determine its carcinogenic potential. The biopsies and tissue comparisons are preferably repeated at regular intervals as determined by one skilled in the art to monitor the progression of the disease in adjacent tissues or the response of the patient to treatment.

The invention claimed is:

1. An isolated antigenic peptide selected from the group consisting of: SEQ ID NO: 6; SEQ ID NO: 7; SEQ ID NO: 8; SEQ ID NO: 9; SEQ ID NO: 10; and SEQ ID NO: 11.

* * * * *